US011041182B2

(12) United States Patent
Wang et al.

(10) Patent No.: US 11,041,182 B2
(45) Date of Patent: *Jun. 22, 2021

(54) METHOD FOR SYNTHESIZING SELECTIVELY LABELED RNA

(71) Applicants: THE GOVERNMENT OF THE UNITED STATES OF AMERICA, AS REPRESENTED BY THE SECRETARY, DEPARTMENT OF HEALTH AND HUMAN SERVICES, Rockville, MD (US); The Board of Regents of the University of Texas System, Austin, TX (US)

(72) Inventors: Yun-Xing Wang, Frederick, MD (US); Yu Liu, Frederick, MD (US); Rui Sousa, San Antonio, TX (US)

(73) Assignees: The Government of the United States of America, Rockville, MD (US); The Board of Regents of the University of Texas System, Austin, TX (US)

( * ) Notice: Subject to any disclaimer, the term of this patent is extended or adjusted under 35 U.S.C. 154(b) by 106 days.

This patent is subject to a terminal disclaimer.

(21) Appl. No.: 16/258,021

(22) Filed: Jan. 25, 2019

(65) Prior Publication Data
US 2019/0241920 A1 Aug. 8, 2019

Related U.S. Application Data

(63) Continuation of application No. 14/903,738, filed as application No. PCT/US2014/045784 on Jul. 8, 2014, now Pat. No. 10,190,143.

(60) Provisional application No. 61/843,864, filed on Jul. 8, 2013.

(51) Int. Cl.
*C12P 19/34* (2006.01)
*C12Q 1/6844* (2018.01)

(52) U.S. Cl.
CPC ............ *C12P 19/34* (2013.01); *C12Q 1/6844* (2013.01)

(58) Field of Classification Search
None
See application file for complete search history.

(56) References Cited

U.S. PATENT DOCUMENTS 5,466,586 A 11/1995 Davey et al.
7,229,799 B2 6/2007 Williams

FOREIGN PATENT DOCUMENTS

WO WO 2012/038448 3/2012

OTHER PUBLICATIONS

Guajardo et al., "A model for the mechanism of polymerase translocation" *Journal of Molecular Biology*, 1997, 265(1):8-19.
Huang et al., "Selective labeling and detection of specific RNAs in an RNA mixture" *Analytical Biochemistry*, 2003, 315(1):129-133.
International Preliminary Report on Patentability issued in PCT/US2014/045784, dated Jan. 12, 2016.
International Search Report and Written Opinion issued in PCT/US2014/045784, dated Oct. 28, 2014.

*Primary Examiner* — Samuel C Woolwine

(57) ABSTRACT

The invention relates to a method for synthesizing a selectively labeled RNA, and an apparatus for performing the method. Specific segments or discrete residues within the RNA may be selectively labeled, and different segments may include different labels.

5 Claims, 18 Drawing Sheets
Specification includes a Sequence Listing.

FIGURE 8
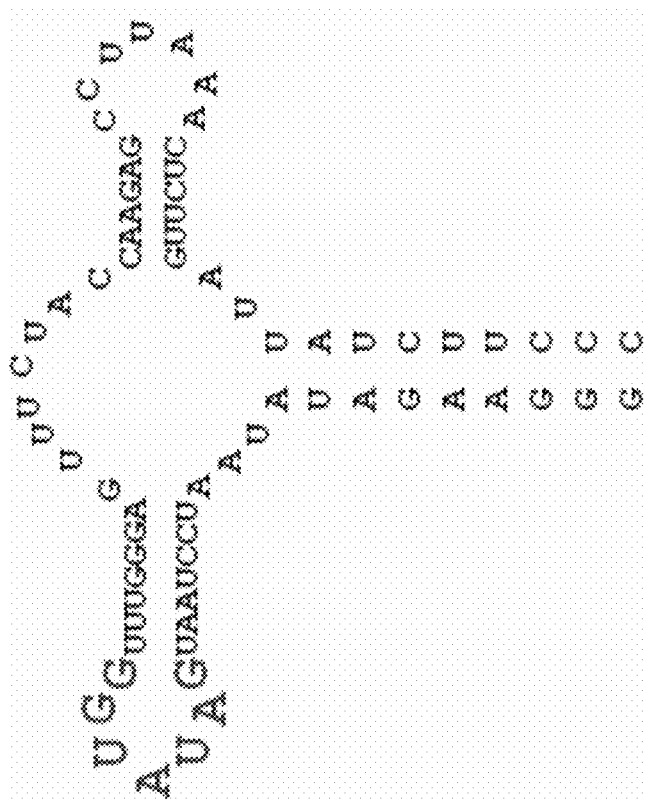
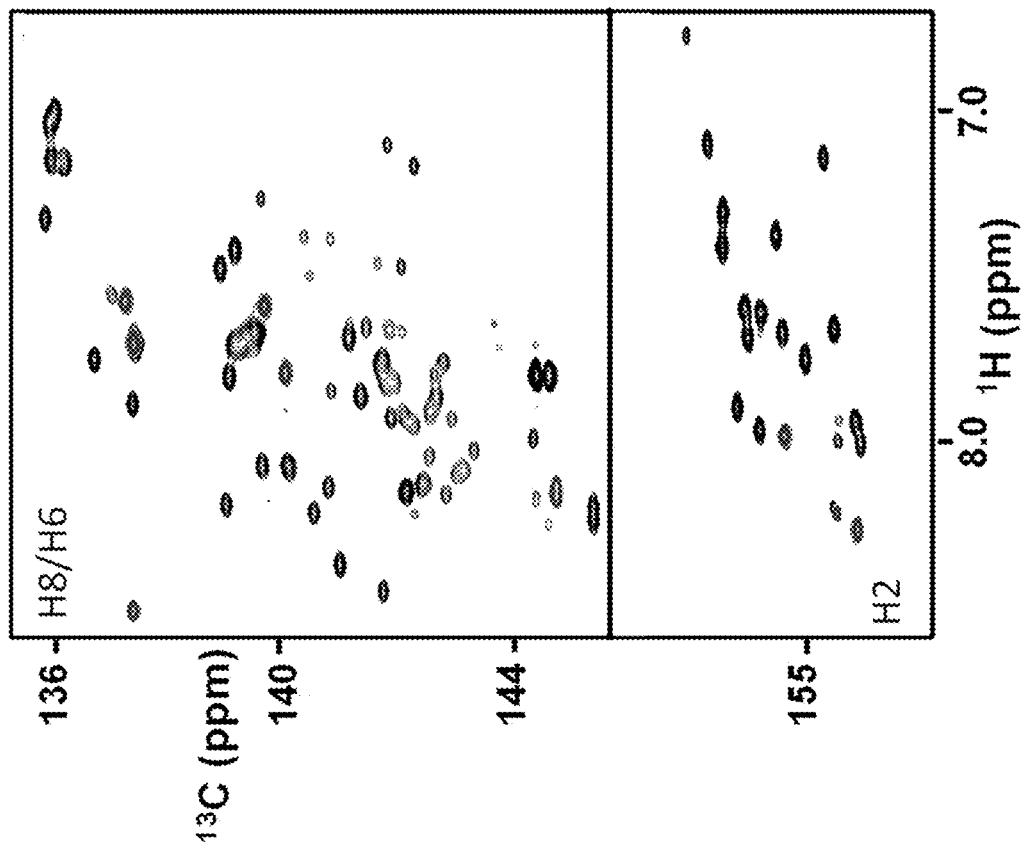

SEQUENCE LISTING

<160> NUMBER OF SEQ ID NOS: 1

<210> SEQ ID NO 1
<211> LENGTH: 71
<212> TYPE: RNA
<213> ORGANISM: Artificial Sequence
<220> FEATURE:
<223> OTHER INFORMATION: synthetic oligonucleotide

<400> SEQUENCE: 1
gggaagauau aauccuaaug auaugguuug ggaguuucua ccaagagccu uaaacucuug    60
auuaucuucc c                                                        71

METHOD FOR SYNTHESIZING SELECTIVELY LABELED RNA

CROSS-REFERENCE TO RELATED APPLICATION

This application is a continuation of U.S. patent application Ser. No. 14/903,738, filed Jan. 8, 2016 which is a national phase application under 35 U.S.C. § 371 of International Application No. PCT/US2014/045784, filed Jul. 8, 2014 which claims priority to U.S. Provisional Application Ser. No. 61/843,864 filed Jul. 8, 2013, each of which is incorporated here by reference in its entirety.

FIELD OF THE INVENTION

The present invention relates to a method for synthesizing a selectively labeled RNA and an apparatus for performing the method.

BACKGROUND OF THE INVENTION

There are mainly two methods for generating RNA molecules. They are 1) solution-phase based in vitro transcription using T7 phage RNA polymerase (hereafter referred as solution-based T7 transcription), and 2) solid-phase based chemical synthesis from phosphoramidites using a synthesizer. Solution-based T7 transcription has widely been used to generate transcript RNAs as large as several kilobases in large quantity, but is not applicable for generating specifically labeled RNAs. Chemical synthesis is used to obtain small RNAs (up to 40-60 bases long) in minute quantity, limited by an intrinsically low coupling rate compared to the DNA counterpart. It is possible to use the chemical synthesis method to generate selective labeled small RNAs, provided that all labeling reagents are commercially available. But specifically labeling sizable RNAs using the chemical synthesis is not practical, due an extremely low efficiency and prohibitively high cost.

Selective labeling of specific residue(s) and/or specific region(s) of RNAs (SLOR) is now possible due to the development of the SLOR technology. The same type of labeling has not yet become practical even for DNA and proteins. Provided herein is a hybrid solid-liquid phase enzymatic method that allows specific labeling at designated residue(s) and/or segment(s) of an RNA. Selected residues can be specifically labeled with stable isotopes such as $^{13}C/^{15}N$, or with fluorophores such as Cy3 and Cy5 rCTP, rUTP, or rNTP derivatives. The efficiency of the method is similar to that using the solution-phase T7 transcription.

SUMMARY OF THE INVENTION

Provided herein is a method for synthesizing a RNA, which may comprise performing an initiation stage, an elongation stage, and a termination stage. The initiation stage may comprise (i) providing a solid phase comprising a DNA template, wherein the DNA is attached to a solid substrate; (ii) providing a first liquid phase comprising a RNA polymerase and ribonucleoside triphosphates (rNTPs); (iii) mixing the solid phase and first liquid phase; (iv) incubating the solid phase and first liquid phase at 4-37° C. for at least 10 minutes to initiate synthesis of the RNA; (v) pausing the RNA synthesis by incubating the solid phase and first liquid phase at 0-5° C. for at least 10 minutes, whereupon the solid phase comprises the RNA polymerase and the RNA being synthesized; and (vi) separating the solid phase from the first liquid phase.

The elongation stage may comprise (i) providing a second liquid phase comprising rNTPs; (ii) mixing the solid phase and second liquid phase; (iii) incubating the solid phase and second liquid phase at 4-37° C. for at least 10 minutes to elongate the RNA; (iv) pausing the RNA synthesis by incubating the solid phase and second liquid phase at 0-5° C. for at least 10 minutes; (v) separating the solid phase from the second liquid phase; and (vi) repeating steps (i)-(v) of part (b) n times, wherein n is equal to 1-100, and wherein the rNTPs in the second liquid phase are the same or different in each repeat. The termination stage may comprise (i) providing a third liquid phase comprising rNTPs; (ii) mixing the solid phase with the third liquid phase; (iii) incubating the solid phase and third liquid phase at 4-37° C. for at least 10 minutes; and (iv) pausing the RNA synthesis by incubating the solid phase and third liquid phase at at 0° C. for at least 10 minutes. The initiation, elongation, and termination stages may be repeated m times, wherein m is equal to 1-100. The rNTPs of at least one of the first liquid phase, the second liquid phase, or third liquid phase may comprise a label.

The DNA may have a density of 30-80% on the solid substrate, and the solid substrate may be a bead. The bead may comprise a gel, glass, or a synthetic polymer. The bead may have a diameter of 5-100 μm. The concentration of DNA may be 30 μm-1 nm. The concentration of rNTP may be 1-100 times the DNA concentration. The RNA polymerase may be a T7 RNA polymerase. The label may be $^{13}C/^{15}N$, $^2H$, Cy3, Cy5, a fluorophore, a heavy atom, or a chemical modification.

BRIEF DESCRIPTION OF THE DRAWINGS

FIG. 8 shows a RNA (SEQ ID NO:1) synthesized as disclosed herein containing a segment selectively labeled with $^{13}C/^{15}N$ nucleotides at nt 20-26, and HSQC 2D NMR spectra associated therewith.

DETAILED DESCRIPTION

Figure 1:
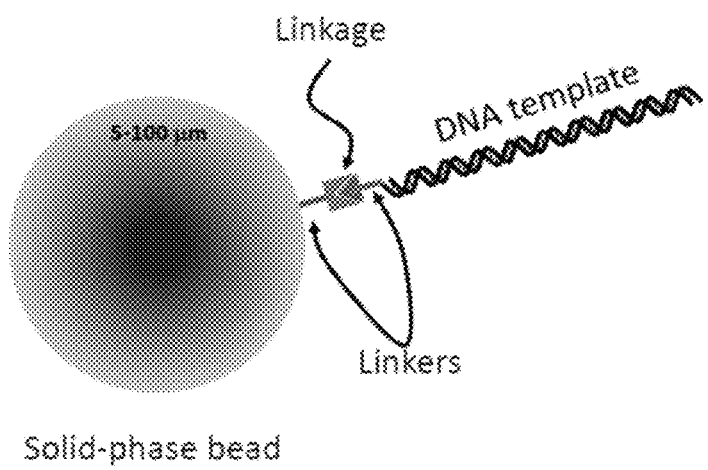
FIG. 1 shows an illustration of the DNA template attached to a solid substrate.

The inventors have discovered/developed a technology of synthesizing a RNA that contains selectively labeled segment(s) or discrete position(s) within the RNA. The method/technology relies on the use of a hybrid solid-liquid phase RNA polymerase transcription reaction. The RNA products synthesized as described herein may be critical reagents for wide applications, such as structural studies using NMR, determining phase in X-ray crystallography, RNA-aptamer-based detection of substances, bacteria or viral particles or disease diagnosis.

Surprisingly, the inventors have found that a ternary complex between a solid substrate-bound DNA template, a RNA polymerase, and a RNA being synthesized from the template can be stabilized so that a RNA synthesis reaction can be paused, and the solid and liquid phase can be separated. The pause can be made to occur at a particular position within the RNA being synthesized by controlling the mixture of NTPs within a liquid reaction mixture being added to the synthesis reaction, and by lowering the temperature of the reaction. For example, the synthesis can be paused just before a U that would otherwise be added to the synthesized RNA based on the DNA template, by adding a reaction mixture containing rATP, rCTP, and rGTP, but not rUTP. Different mixtures of rNTP can be used to selectively synthesize segment(s) and/or position(s) within the RNA.

After the reaction is paused, the liquid phase containing unreacted rNTPs can be separated from the solid phase comprising the ternary complex, and then washed away. A liquid reaction containing a different set of rNTPs can then be added to continue synthesizing the RNA in the next step. During the elongation, any step can be paused, and the liquid phase washed away. The elongation step can then be continued by adding a new liquid phase containing a new mixture of rNTPs. Each liquid reaction mixture added during each segment of the elongation step can include a different mixture of rNTPs with different labels, so that the resulting RNA contains different segments that are labeled differently. Unexpectedly and counter-intuitively, the concentration of rNTPs used in the RNA synthesis reactions is not in the millimolar range as is typically used in conventional in vitro transcription, but rather in the micromolar range. Accordingly, rNTPs are used at approximately stoichiometric concentrations in comparison to the DNA template. Higher concentrations may be inhibitory. In addition, the inventors have surprisingly discovered that the RNA synthesis reaction must be gently mixed so as not to produce bubbles/forms, and thus, if performed in an automated fashion, may be slowly rotated 360°, and not mixed by stirring, shaking, or bubbling as is typically done in the art.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

rNTPs as used herein may refer to a labeled or non-labeled, derivatized or non-derivatized, ribonucleoside triphosphate.

2. Method for Selectively Labeling RNA

Provided herein is a method for selectively labeling a RNA by synthesizing the RNA from a DNA template using a RNA polymerase. The RNA may be labeled within a segment, and may be labeled at a discrete position. The method may comprise a hybrid solid-liquid phase reaction. The synthesis reaction may comprise a DNA template, which may be attached to a solid substrate, a RNA polymerase, ribonucleoside triphosphates (rNTPs), which may be labeled and/or derivatized, $Mg^{2+}$, dithiothreitol (DTT), a DNase inhibitor, a RNase inhibitor, and a buffer. The reaction may not include a DNase or a RNase. A liquid reaction mixture of the liquid phase may comprise NTPs, $Mg^{2+}$, DTT, the RNase and/or DNase inhibitors, and a buffer. The method may comprise an initiation step, an elongation step, and a termination step. One or more of these steps may be paused by changing the temperature of the reaction, or by including a particular combination of rNTPs in the reaction. Without being bound to a particular theory, the reaction may be paused by stabilizing a ternary complex comprising the RNA polymerase, the DNA template, and the RNA being synthesized. The pause may be initiated by virtue of a rNTP being missing from the liquid phase, so that RNA synthesis cannot proceed past a particular position at the DNA template. While the reaction is paused, a first liquid reaction mixture may be removed or separated from the solid phase, and a second liquid reaction mixture may be added. The first and second liquid reaction mixtures may comprise different combinations of rNTPs, such that the rNTPs in the two reaction mixtures may comprise different rNTP labels, or such that one comprises a label and the other does not. The paused step may be restarted by changing the reaction temperature or by changing the combination of rNTPs in the reaction.

a. Reagents (1) Solid Phase

The RNA synthesis reaction may comprise a solid phase, which may comprise a DNA template attached to a solid substrate. The solid substrate may be a gel, glass, a polystyrene, or a synthetic polymer. The solid substrate may have a size of 5-100 μm, and may also have a size of 5-10, 5-20, 10-20, 10-50, 20-50, 20-70, 30-80, 40-100, 50-100, 70-100, or 80-100 μm. The solid substrate may be a bead. During the synthesis reaction, the solid phase may further comprise the RNA polymerase and the RNA being synthesized. The solid phase may comprise a DNase or RNase inhibitor, and may not include a DNase or RNase.

The DNA template may be attached to the solid substrate with an affinity-based linkage, a covalent linkage, or any other linkage known in the art. The linkage may be non-reactive, stable in the presence of a reducing agent, and stable at a temperature of about 0-40° C., and may have a very low retention rate. The affinity-based linkage may be a biotin-avidin linkage, or any other affinity-based linkage known in the art. The avidin may be avidin, streptavidin or NEUTRAVIDIN®. The NEUTRAVIDIN® may be a deglycosylated form of avidin from egg whites, with a mass of approximately 60,000 daltons, and from which excess carbohydrate has been removed. The biotin may be attached to the DNA template or to solid substrate, and the avidin may be attached to the solid substrate or DNA template, respectively. The covalent linkage may be through an amino reaction, a thiol reaction, or any other chemistry known in the art. The covalent linkage may also be a flexible and soluble organic chain molecule, which may be polyethylene glycol (PEG). An example of the solid substrate-DNA template linkage is shown in FIG. 1.

The DNA template may have density on the solid substrate of 30-80%, 30-40%, 30-50%, 40-50%, 40-60%, 50-70%, 50-80%, or 70-80%. The density may balance minimization of steric hindrance and maximization of the density of accessible templates. The DNA concentration may be 1-100, 1-80, 1-50, 1-30, 5-100, 5-80, 5-50, 5-30, 5-28, 10-100, 10-80, 10-50, 10-30, 20-100, 20-80, 20-50, 20-30, 40-100, 40-80, or 50-100 μM. The DNA concentration may also be 1-10, 5-10, 5-20, 10-20, 10-50, 20-50, 20-100, or 50-100 nM, or 30 μM-1 nM.

(2) Liquid Reaction Mixture

The liquid reaction mixture may comprise a rNTP, which may be rATP, rGTP, rCTP, or rUTP. The rNTP may comprise a label, which may be a radiolabel or a fluorophore. The label may also be a heavy atom or a chemical modification. The radiolabel may be deuterium, $^{13}C$, $^{13}C/^{15}N$, $^{2}H$, $^{32}P$, $^{35}S$, $^{8-14}C$, or any other label known in the art. The fluorophore may be Cy3, Cy5, Cy5.5, fluorescein, FAM-6, DY490, DY547, DY549, DY647, DY649, DY677, Cy2, Alexa 488, Alexa 546, Alexa 555, TAMRA, WellRED D4, or WellRED D3, or any other fluorophore known in the art. The rNTP may also comprise an aminoallyl group, and may be labeled by an amine-reactive fluorescent dye, biotin, or hapten. The amino-reactive may be Fluorophore, Methoxycoumarin, Dansyl, Pyrene, Alexa Fluor 350, AMCA, Marina Blue dye, Dapoxyl dye, Dialkylaminocoumarin, Bimane, Hydroxycoumarin, Cascade Blue dye, Pacific Orange dye, Alexa Fluor 405, Cascade Yellow dye, Pacific Blue dye, PyMPO, Alexa Fluor 430, NBD, QSY 35, Fluorescein, Alexa Fluor 488, Oregon Green 488, BODIPY 493/503, Rhodamine Green dye, BODIPY FL, 2',7'-Dichloro-fluorescein, Oregon Green 514, Alexa Fluor 514, 4',5'-Dichloro-2',7'-dimethoxy-fluorescein (JOE), Eosin, Rhodamine 6G, BODIPY R6G, Alexa Fluor 532, BODIPY 530/550, BODIPY TMR, Alexa Fluor 555, Tetramethyl-rhodamine (TMR), Alexa Fluor 546, BODIPY 558/568, QSY 7, QSY 9, BODIPY 564/570, Lissamine rhodamine B, Rhodamine Red dye, BODIPY 576/589, Alexa Fluor 568, X-rhodamine, BODIPY 581/591, BODIPY TR, Alexa Fluor 594, Texas Red dye, Naphthofluorescein, Alexa Fluor 610, BODIPY 630/650, Malachite green, Alexa Fluor 633, Alexa Fluor 635, BODIPY 650/665, Alexa Fluor 647, QSY 21, Alexa Fluor 660, Alexa Fluor 680, Alexa Fluor 700, Alexa Fluor 750, or Alexa Fluor 790, or any other amine-reactive dye known in the art. The rNTP may also be a rNTP derivative. The rNTP derivative may comprise a heavy atom, or any other derivative known in the art. A rNTP herein may be incorporated into the RNA by SLOR. The RNA may thus be used as a RNA-based reagent for detection and imaging. A rNTP herein may also be incorporated into the RNA for determining phase in X-ray crystallography.

The concentration of the rNTP may be approximately stoichiometric with the DNA concentration, and may be at a micromolar scale. The rNTP concentration may be 1, 2, 3, 4, 5, 6, 7, 8, 9, 9.6, 10, 96, 1-200, 1-150, 1-100, 1-50, 1-10, 20-200, 20-150, 20-50 times the DNA concentration. The rNTP may be dissolved in a buffer and may have a pH of 7.5-8.5, 7.5-8.1, 7.9-8.5, 7.9-8.2, or 8.0-8.2.

The liquid reaction mixture may comprise the RNA polymerase. The RNA polymerase, may be a T7 RNA polymerase, a T4 RNA polymerase, a T3 RNA polymerase, or a SP6 RNA polymerase. The concentration of RNA polymerase may be about equal to or higher than the DNA concentration. The liquid reaction mixture may comprise a DNase or RNase inhibitor, and may not include a DNase or RNase.

The liquid reaction mixture may comprise $Mg^{2+}$. The $Mg^{2+}$ concentration may be about 1-50 mM, 10-50 mM, 10-30 mM, 20-30 mM, 20-25 mM, or 20-50 mM. The DTT concentration may be about 1-10 mM, 2-10 mM, 5-10 mM, 5 mM, or 10 mM.

The liquid reaction mixture may comprise a buffer. The buffer may comprise a Tris-saline buffer. The buffer may comprise buffer B, which may comprise 100 mM Tris-HCl, 100 mM $K_2SO_4$, 6-25 mM $MgSO_4$, 10 mM DTT, pH 7.9. The buffer may also comprise buffer C, which may comprise 100 mM Tris-HCl, 6-25 mM $MgSO_4$, pH 7.9. The buffer may also comprise buffer D, which may comprise 100 mM Tris-HCl, 6-25 mM $MgSO_4$, 10 mM DTT, pH 7.9. The liquid reaction mixture may have a pH of about 7.5-8.5, 7.5-8.1, 7.9-8.5, 7.0-8.2, 7.9-8.2, or 8.0-8.2.

b. RNA Synthesis Reaction

Figure 2:
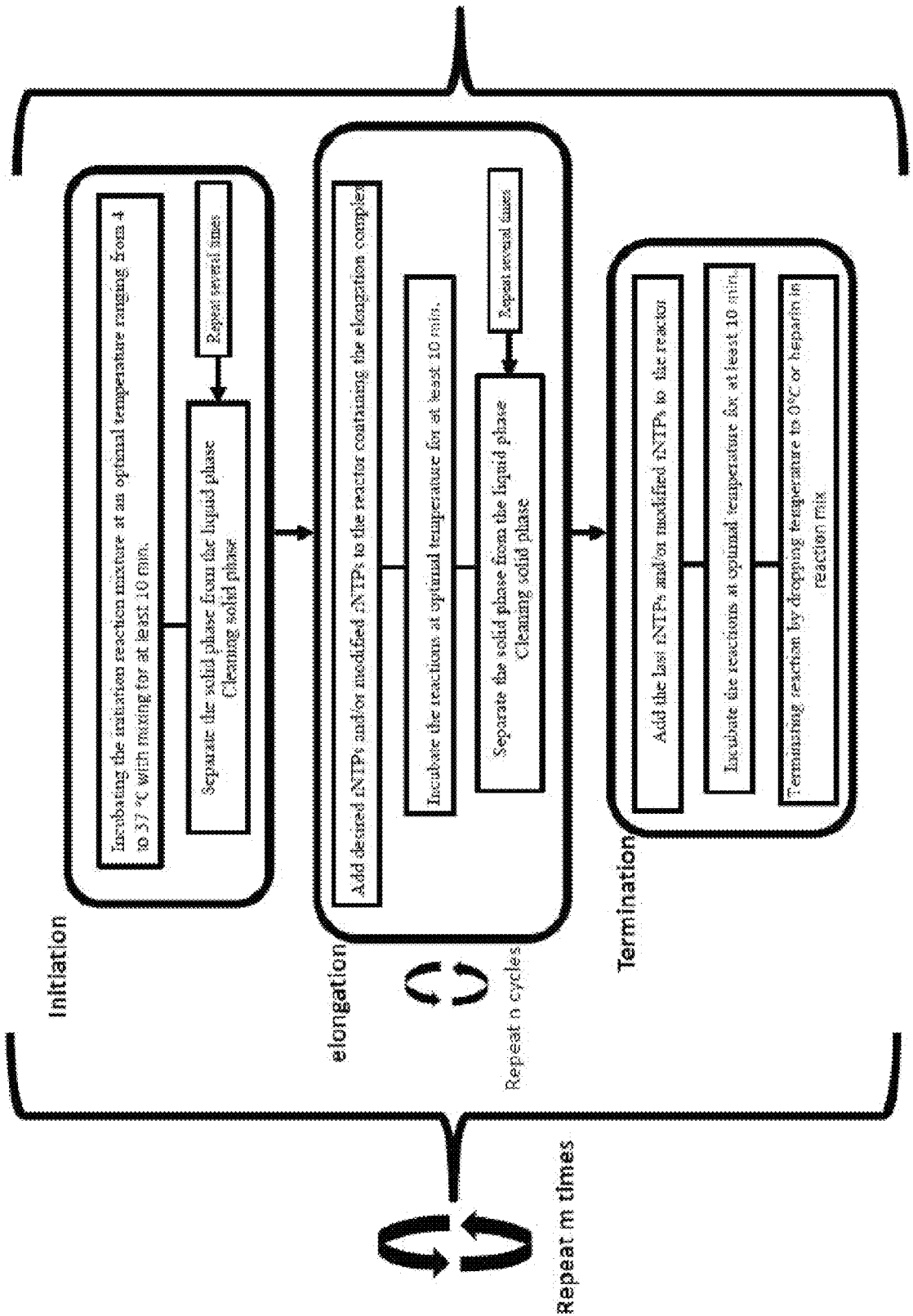
FIG. 2 shows an outline of the steps and cycles of a hybrid solid-liquid reaction for selectively labeling RNA. The reaction process may be divided into three stages: initiation, elongation and termination, among which elongation is further divided into multiple steps (n cycles), depending on the length of the RNA to be synthesized and the labeling scheme. The whole process can be repeated m times, depending on the amount of RNA to be synthesized and the amount of the solid-phase DNA templates available. This process can be carried out by hands or by an automated RNA synthesizer.
Figure 3:
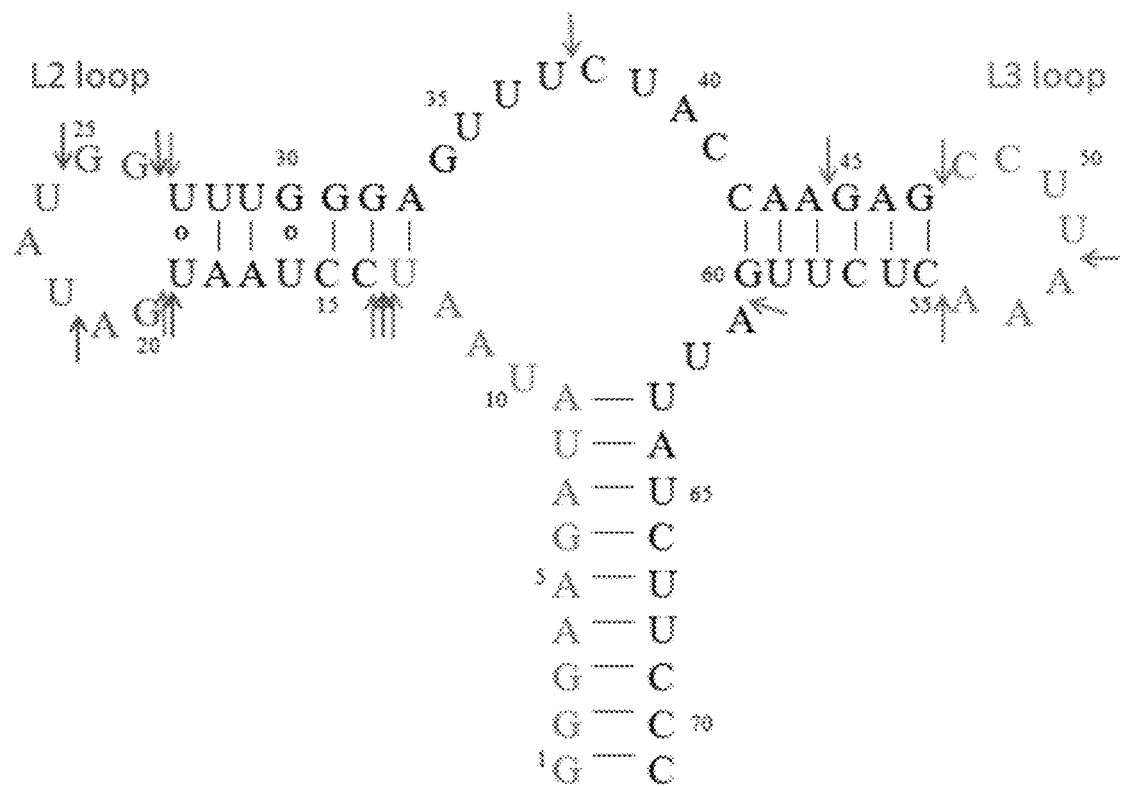
FIG. 3 shows the secondary structure of an adenine riboswitch RNA (SEQ ID NO:1) (71 nt). Seven (7) site-specifically labeled riboswitch RNA samples were synthesized by the selectively labeled RNA synthesis method disclosed herein (FIGS. 7-13). These are: the isotope-labeled sites of the three samples are nt 1-13 (FIG. 7), nt 20-26 (FIG. 8), nt 34-41 (FIG. 9) and nt 48-55 (FIG. 10), respectively. Labeling at discrete positions (nt 21, 38, 39) (FIG. 11) and at a single position (nt 39) (FIG. 12) are also demonstrated. The pause positions among the transcriptions are marked by arrows.

The RNA synthesis reaction may comprise an initiation stage, an elongation stage, and a termination stage. The three stages may be performed as cycle multiple times, and the elongation stage may be performed multiple times within a cycle. An example of the reaction is shown in FIG. 2.

(1) Initiation Stage

The initiation stage may comprise gently mixing an initiation stage reaction mixture, which may comprise a liquid reaction mixture. The initiation stage reaction mixture may also comprise the RNA polymerase, rNTPs, and solid phase. The rNTPs may be not include a specific type of rNTP, which may be rATP, rCTP, rGTP, or rUTP, such that RNA synthesis cannot proceed beyond a specific nucleotide in the DNA template by virtue of the absence of the missing rNTP, which would otherwise be added and allow the synthesis to continue. The initiation stage reaction mixture may be incubated at a temperature of about 0-37, 0-40, 4-40, 4-37, 4-25, 5-25, 5-37, 10-40, 10-37, 10-25, or 37° C. The initiation stage reaction may be performed for about 5-30, 5-20, 5-15, 10-30, 10-20, 10-15, 20-30, 10, 20, 30, 40, 50, 60 minutes, or at least 10 or 60 minutes. The RNA synthesized during the initiation stage may be at least 5, 6, 7, 8, 9, 10, 11, 12, 13, 14, 15, 16, 17, 18, 19, or 20 nucleotides in length, which may stabilize an initiation ternary complex, which may comprise the solid phase, the RNA polymerase, and the RNA being synthesized. If the RNA synthesized during the initiation stage is longer, such as at least 13, 14, or 15 nucleotides in length, the initiation ternary complex may be more stable, and the RNA synthesis more efficient.

Upon formation of an initiation ternary complex, the solid phase may be separated from the liquid phase, and may be washed using a buffer as disclosed herein. The washing may be performed at a temperature of about 0, 1, 2, 3, 4, 5, 0-4, or 0-5° C. The solid phase may be separated from the liquid reaction mixture and washed several times, which may be at least 2, 3, 4, 5 times, or 1-10, 1-20, 5-10, 5-20, or 10-20 times. The reaction may be paused at a temperature of about 0, 1, 2, 3, 4, 5, or 0-4° C. for 5-30, 5-20, 5-15, 10-30, 10-20, 10-15, 20-30, 10, 20, 30, 40, 50, or 60 minutes, or at least 10 or 60 minutes, or as many as 24-48 hours.

(2) Elongation Stages

The RNA synthesis reaction may comprise an elongation stage. The elongation stage may comprise adding a liquid reaction mixture to the initiation stage reaction mixture. The rNTPs in the liquid reaction mixture may comprise a different combination of rNTPs, or a different set of labels, as compared to the initiation reaction mixture. The mixture of rNTPs may depend on the sequence of the DNA template, and the segment of the RNA being synthesized that is desired to be labeled or unlabeled, as the case may be. The rNTP mixture in each liquid reaction mixture may not include a specific type of rNTP, which may be rATP, rCTP, rGTP, or rUTP, such that RNA synthesis cannot proceed beyond a specific nucleotide in the DNA template by virtue of the absence of the missing rNTP, which would otherwise be added and allow the synthesis to continue. This may cause the RNA synthesis reaction to pause. The RNA synthesis reaction may also comprise multiple elongation stages, and the rNTP mixture in the liquid reaction mixture used in each elongation stage may be different, depending on the DNA template sequence and the desired labeling for a particular segment of the RNA being synthesized.

The reaction mixture may be incubated at a temperature of about 0, 1, 2, 3, 4, 0-37, 0-40, 4-40, 4-37, 4-25, 5-25, 5-37, 10-40, 10-37, 10-25, or 37° C., for about 5-30, 5-20, 5-15, 10-30, 10-20, 10-15, 20-30, 10, 20, 30, 40, 50, 60 minutes, or at least 10 or 60 minutes. In particular, the reaction mixture may be incubated at about 0, 1, 2, 3, 4, 5-37, 10-25 or 25° C. Incubating the reaction mixture at about 0, 1, 2, 3, 4, 5, 0-4, or 0-5° C. may cause the RNA synthesis reaction to pause. The solid phase may then be separated from the liquid reaction mixture, and the solid phase may be washed using a buffer as disclosed herein. The washing may be performed at a temperature of about 0, 1, 2, 3, 4, 5, 0-4, or 0-5° C. The solid phase may be separated from the liquid reaction mixture and washed several times, which may be at least 2, 3, 4, 5 times, or 1-10, 1-20, 5-10, 5-20, or 10-20 times. The elongation stage may be performed multiple times as desired, in order to label different segments of the synthesized RNA differently.

(3) Termination

The RNA synthesis reaction may comprise a termination stage. The termination stage may comprise adding a mixture of rNTPs that is missing the rNTP that is the first nucleotide in the RNA that is synthesized from the DNA template. As an example, a mixture of rATP, rCTP, and rUTP, and excluding rGTP may be added if the first residue in the RNA that is synthesized from the DNA template is a G. This may prevent re-initiation of a new round of RNA synthesis from the DNA template. The termination stage may also comprise adding heparin, or adding rNTPs followed by incubating the reaction at about 0, 1, 2, 3, 4, 5, 0-4, or 0-5° C. The initiation, elongation, and termination stages may be performed multiple times as desired, depending on the desired yield of selectively labeled RNA to be synthesized.

(4) Mixing and Separation

Figure 5:
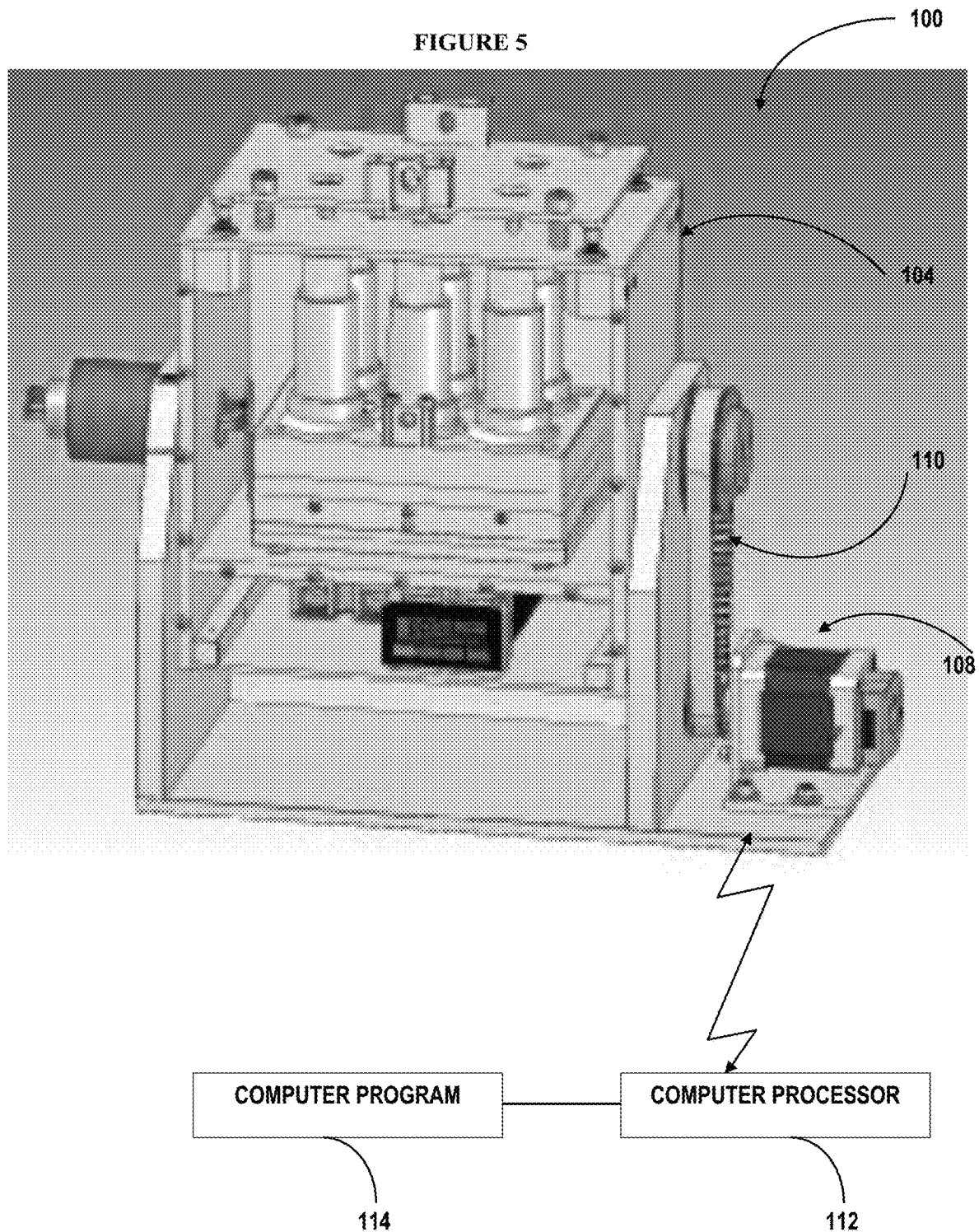
FIG. 5 shows reaction vessels of the apparatus in FIG. 4.

The reaction mixture may be gently mixed at any or all stages of the RNA synthesis reaction, and the mixing may be performed in a reaction vessel 104 (FIG. 5). The reaction vessel 104 may also be manipulated such that the reaction is gently mixed so that the reaction does not form bubbles or forms. For example, the reaction vessel 104 containing the reaction may be gently rotated at certain angles so as to prevent bubbling/forms. The reaction vessel 104 may also be wobbled. The reaction vessel 104 may also be rotated 360 degrees at a slow rate. The reaction vessel may also not be stirred, shaken, or bubbled. The reaction mixture may be mixed under an inert atmosphere at any or all stages of the RNA synthesis reaction.

The solid phase may be separated from the liquid reaction mixture by any means known in the art. The separation may be via centrifugation, magnetic attraction, or filtration, which may be vacuum-driven.

3. Apparatus for Selectively Labeling RNA

Figure 4:
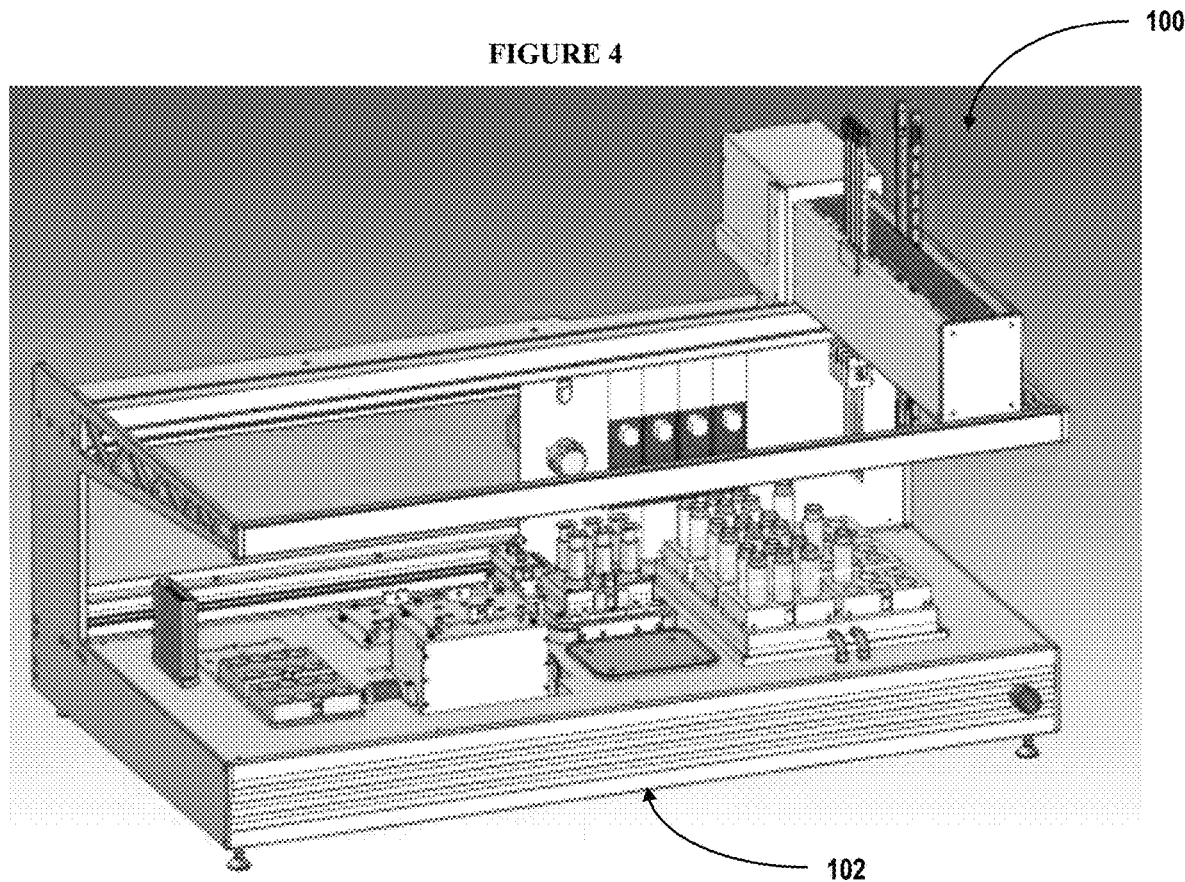
FIG. 4 shows an apparatus/automated platform for performing the RNA synthesis reaction disclosed herein, which may perform a hybrid solid-liquid phase synthesis of RNA. This platform may execute reaction cycles under an inert atmosphere and desired temperatures, and may be automatically driven by a computer program that is executed by a computer processor.

An apparatus, designated 100, is disclosed for selectively labeling RNA. In particular, the apparatus 100 may be an automated platform 102 that performs the method of RNA synthesis disclosed herein, which may comprise performing the initiation stage, elongation stage, and termination stage. Referring to FIGS. 4 and 5, the automated platform 102 may be operatively controlled by a computer program 114 with a user input provided by an individual. In addition, the operations of the computer program 114 are controlled by instructions embodied in the computer program 114 and executed by a computer processor 112 in operative communication with the computer program 114.

Figure 6:
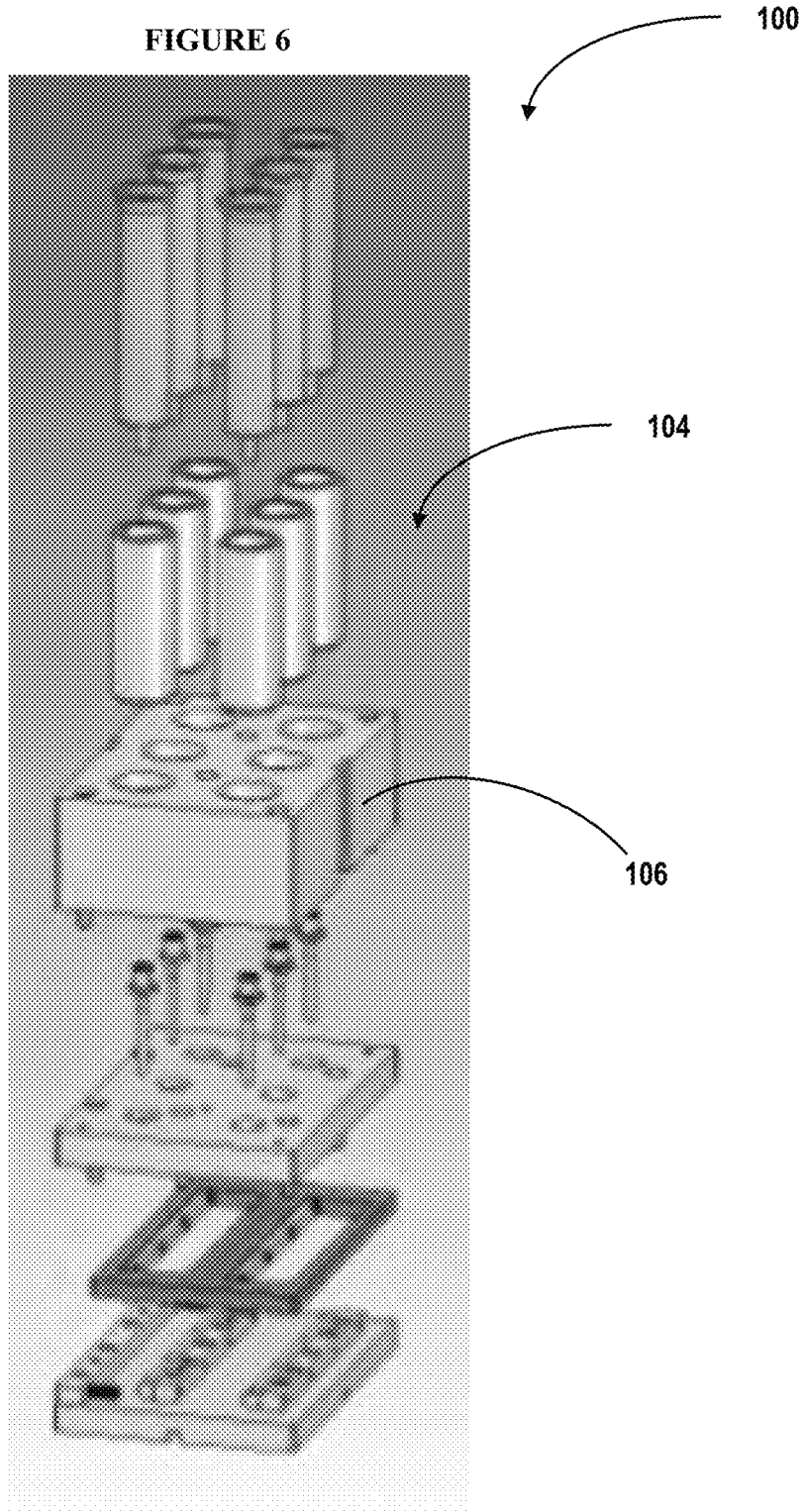
FIG. 6 shows a holder for the reaction vessels in FIG. 5.
Figure 14:
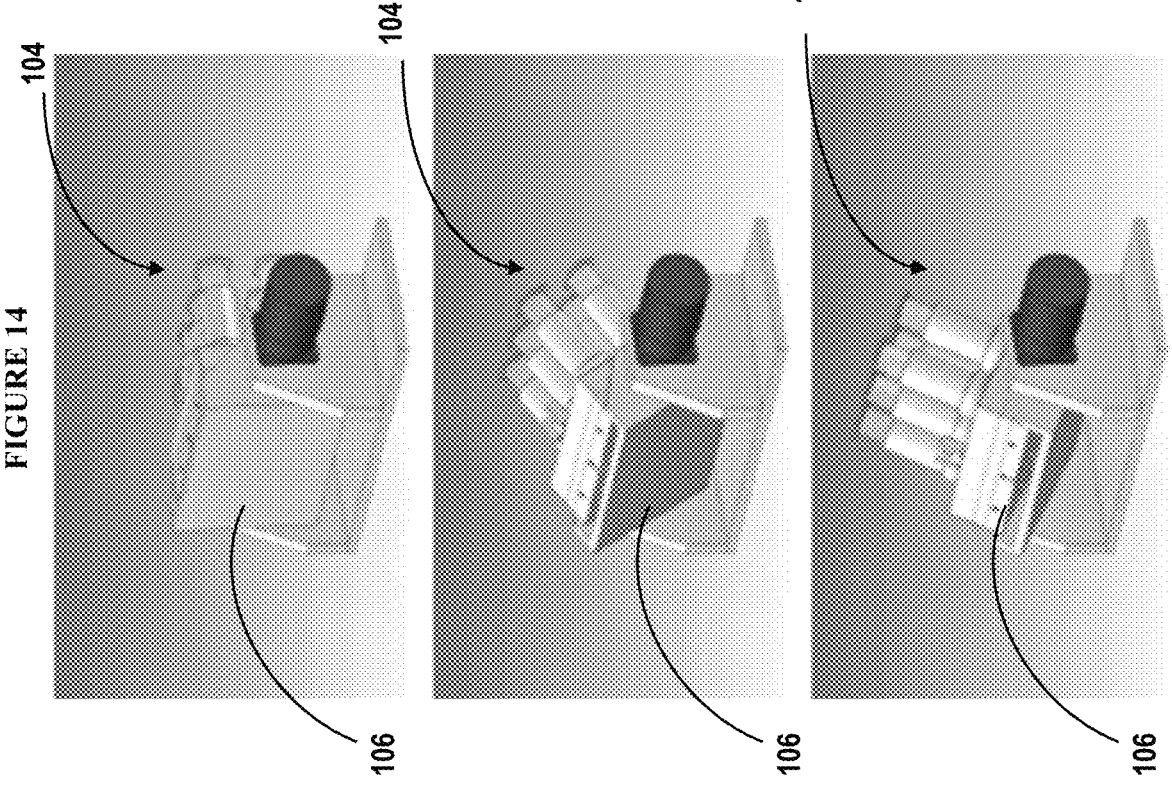
FIGS. 14A-14C illustrate a sequence of view showing the gentle stirring in reaction vessels hosted in a holder of the apparatus.
Figure 16:
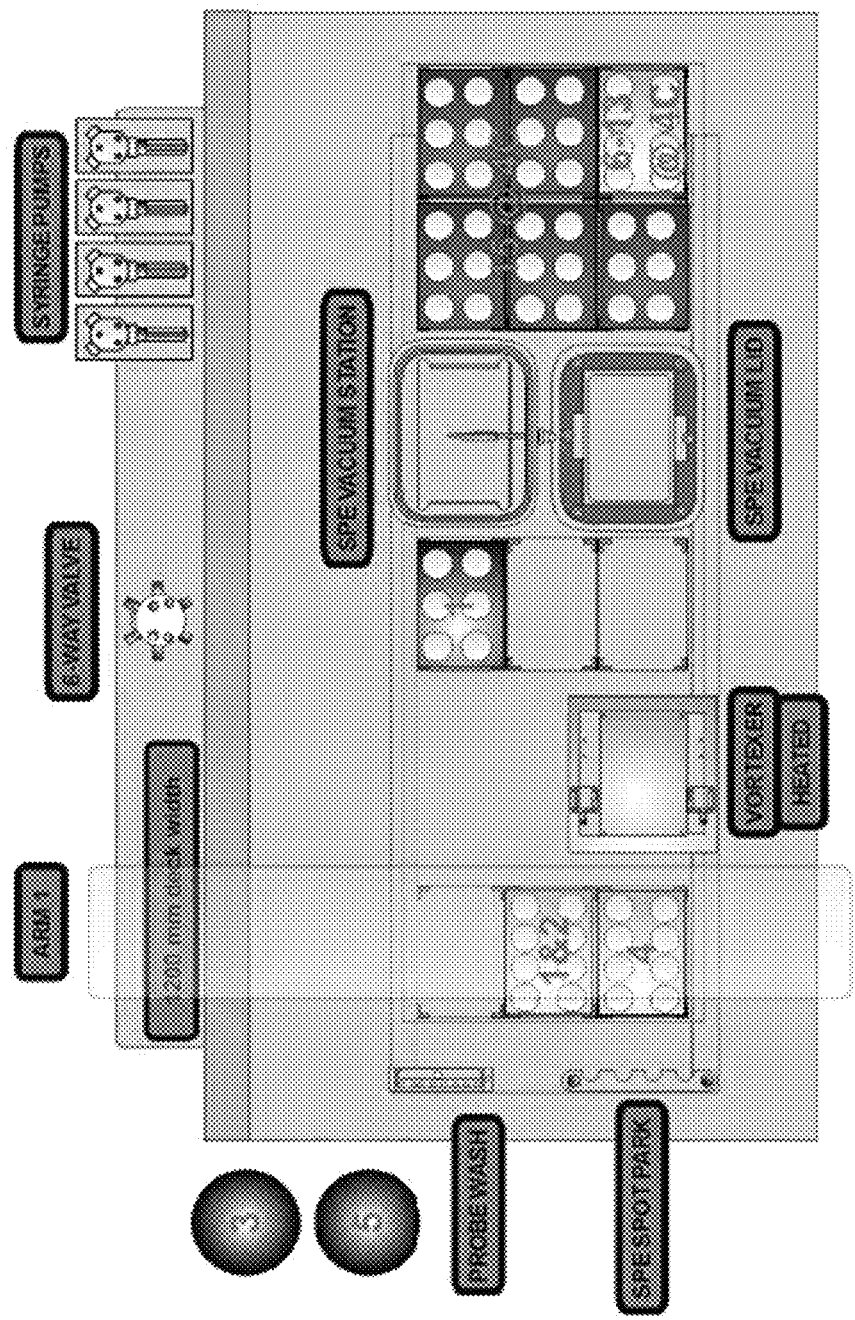
FIG. 16 shows the layout of the deck of an exemplary automated platform for synthesis of a RNA as described herein.
Figure 17:
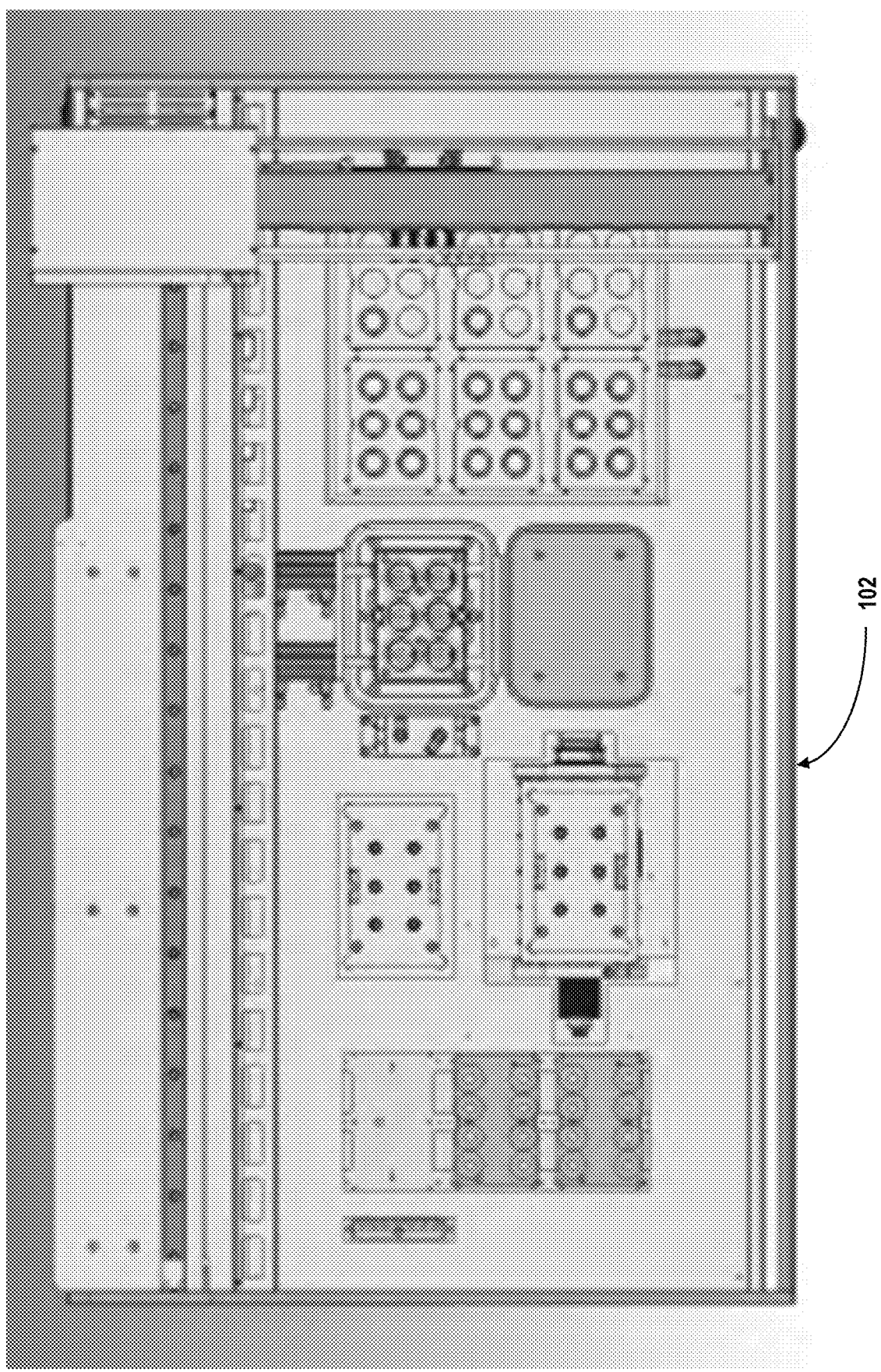
FIG. 17 shows another view of the automated platform disclosed herein.
Figure 18:
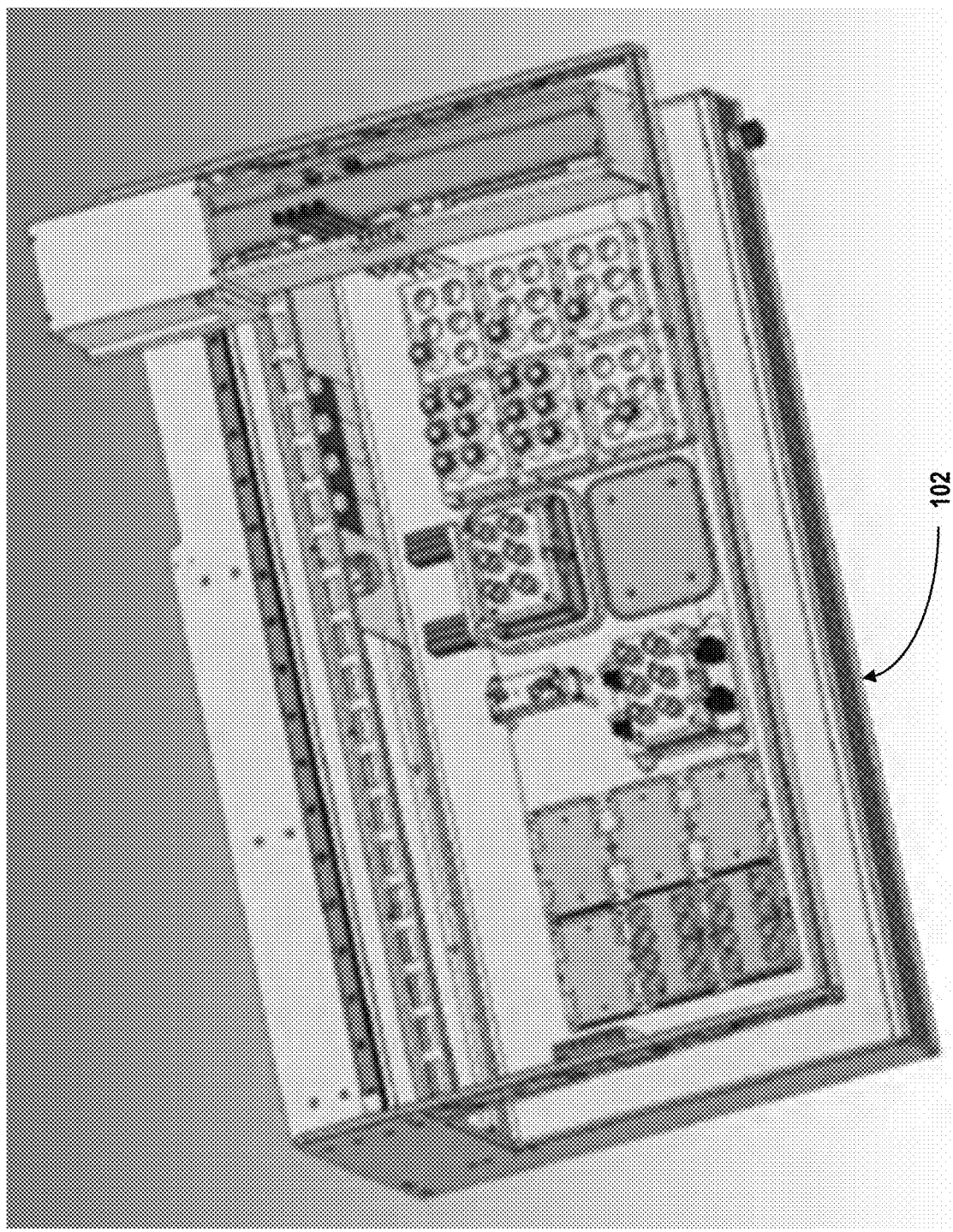
FIG. 18 shows another view of the automated platform disclosed herein

The apparatus 100 may comprise a reaction vessel as disclosed herein. All stages of the RNA synthesis reaction may be performed in the reaction vessel 104. An example of the reaction vessel 104 is shown in FIG. 5. The reaction vessel 104 is in operative association with a motor 108 that manipulates the reaction vessel 104 through a gear arrangement 110 that is operatively engaged with the motor 108. In some embodiments, the motor 108 is also in operative communication with the computer processor 112 for controlling the manipulation of the reaction vessel 104, which may be tumbled, to ensure that the reaction is not stirred, shaken or bubbled. The apparatus 100 may also comprise a holder 106 for receiving and manipulating the reaction vessel 104 as illustrated in FIG. 6. As shown in the sequence of views in FIGS. 14A-14C, the holder 106 may manipulate the reaction vessel 104 in a manner that allows a gentle mixing of the reaction within the reaction vessel that does not form any bubble in the reaction. In some embodiments, the reaction vessel 104 may be rotated 360 degrees at a slow rate by the holder 106 or the reaction vessel 104 may be wobbled by the holder 106. In no instance is the reaction vessel 104 manipulated by the holder 106 such that the reaction vessel 104 stirs, shakes, or bubbles the reaction. FIG. 16 shows the layout of an exemplary deck of the automated platform, and FIGS. 17 and 18 show top-down views at different angles of the automated platform.

The apparatus may comprise: an integrated gripper for transportation of plates, solid phase extraction (SPE)-blocks, opening of a vacuum box, and inserting/extracting receiving plates or racks; stainless steel 2-channel pipetting probes for delivering liquids and gases, which may be done simultaneously, and which may have variable spacing between probes (8-38 mm) for every type of probe; liquid level detection at each probe; precision syringe pumps for liquids (for 500 µL, 1 mL, 2.5 mL, 5 mL syringes) and precision syringe pumps for gas; high speed hotplate vortexers with integrated heating to 37° C. or even higher; 110 V high speed, low noise hotplate vortexers with integrated heating temperature control with pneumatic clamps for an external pressurized air supply (6-8 bar); one portion of a deck of the platform may be kept at 4° C.; at least one set of pressure spots for reactor/filtration vessels; a wash station; a high-flow 6-way valve for six system liquids; a SPE to accommodate the reaction/filtration vials; a holder for pressures spots, which may have at least two positions and be pneumatic; a pulse vacuum which may be software-controlled; positive pressure, which may be software-controlled, and may have two individual channels, with an external pressurized air supply; racks for reaction/filtration vials, and reactor filtration vessels; a work bench (may be 1200×710 mm); and a work area (which may be 1000×290 mm) with a MTP adapter.

The present invention has multiple aspects, illustrated by the following non-limiting examples.

Example 1

Preparation of a Partially Isotope-Labeled RNA by Stepwise Transcription

This example demonstrates the internal labeling of a 71 nucleotide-long RNA ribo-switch RNA by stepwise transcription. The stepwise transcriptions proceed as initiation, elongation, and termination stages. The design of stepwise transcription is flexible, and the reactions are able to be paused at certain stage and continued later, controlled by some factors, including temperature change, and rNTP additions. The transcription system allows a reaction to be moved to the elongation stage after being paused at the initiation stage after the first stretch of residues for at least 24 hr at 4° C. under proper buffer conditions. This makes it possible to synthesize RNA products labeled at different positions. Seven RNA samples that have specific segments or residues labeled with isotope-enriched rNTPs, biotinylated rCTP, or Alexa555 and Alexa488 rUTP derivatives have been obtained by using the stepwise transcription method successfully.

Similar initiation stage was pursued for synthesizing the seven RNA samples which were used in NMR or single molecule FRET studies. Mix immobilized DNA (the final concentrations of DNA vary from 5.0 µM to 28.0 µM) with active T7 RNA polymerase (the concentration of T7 RNA polymerase is equal or higher than that of DNA) in buffer B (100 mM Tris-HCl, 100 mM $K_2SO_4$, 6-25 mM $MgSO_4$, 10 mM DTT, pH=7.9) at a temperature between 10-37° C. The reaction containers for the transcription reactions are 50 mL vacuum-driven filtration system (Millipore, MA). Then, incubate with rATP, rGTP, and rUTP at 37° C. (the types of rNTPs added are dependent on the sequence of the target RNA, and the three types of rNTPs are necessary for synthesizing the first stretch of nucleotides at the 5'-end. And the concentration ratio: rATP or rGTP:DNA=96:1, rUTP:DNA=9.6:1. The ratios among T7, rNTP and DNA are maintained in other RNA sample synthesis, except otherwise noted in this paper.). After 20 mins, the beads were vacuumed and rinsed by buffer C (100 mM Tris-HCl, 6-25 mM $MgSO_4$, pH=7.9) at least 4 times in order to remove residual rNTPs, buffer, abortive or premature RNA, free T7 RNA polymerase, and other reaction ingredient or side products that are not bound with beads. The beads should be dry after vacuum to get rid of residual rNTPs as much as possible, or else may cause the unwanted bypass of the later reaction steps. Procession of properly functional T7 RNA polymerase was paused after synthesizing the first stretch of residues due to lack of rCTP after the initiation step.

In the elongation steps, buffer D (100 mM Tris-HCl, 6-25 mM $MgSO_4$, 10 mM DTT, pH=7.9) with different combinations of rNTPs (all 4 types of rNTPs are not present simultaneously in the reaction mixtures, except sometimes in the last step) are added to the beads used in initiation step. The concentrations of the added rNTPs in the steps of elongation stage are important, and the actually added amount should be not more than the needed amount supposedly the yield is 100% according to stoichiometry. More details for each sample preparation are described in the following parts.

a. Labeling One Segment with $^{13}C^{15}N$-rNTPs and Rest with Deuterate-rNTPs

Figure 7:
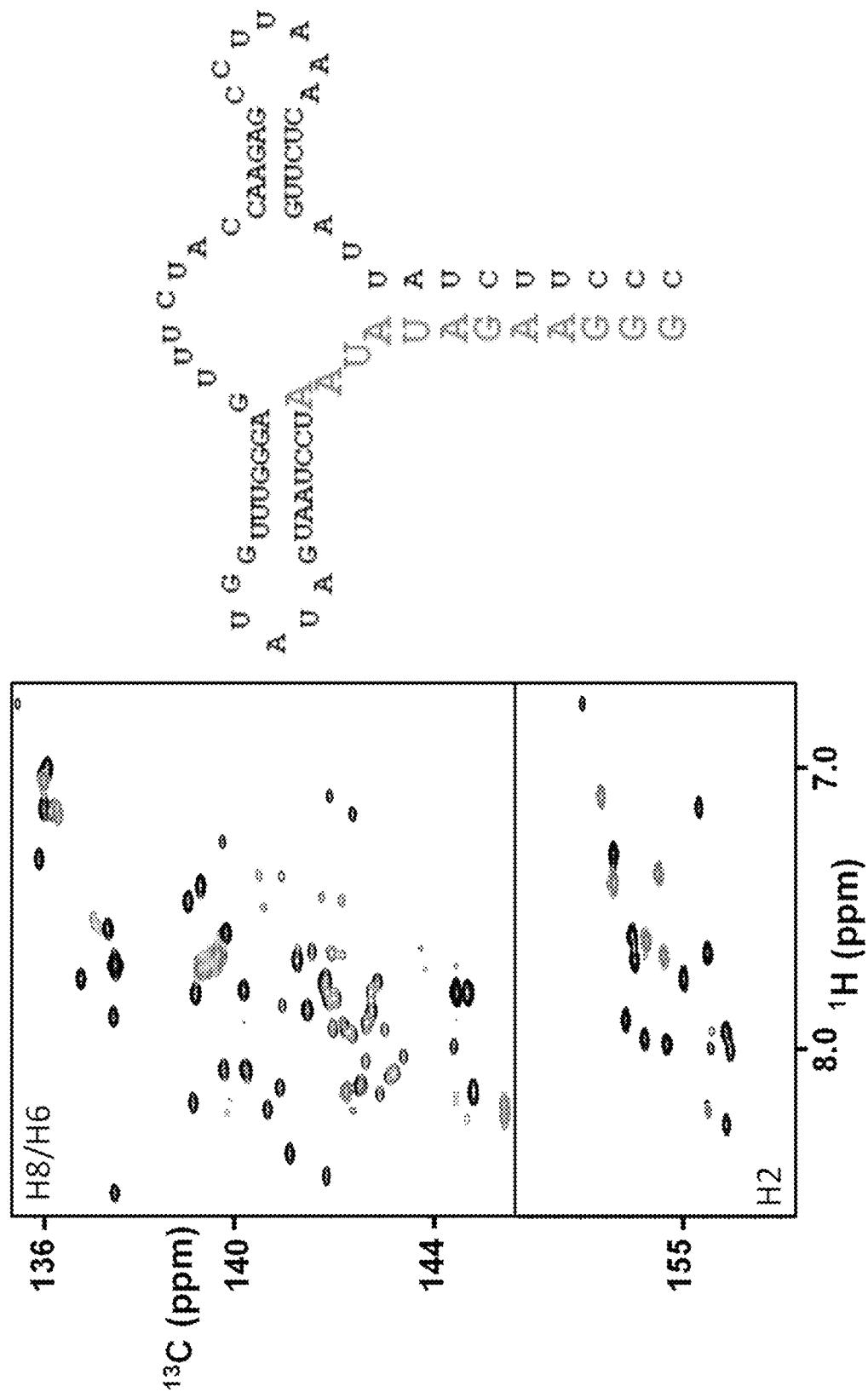
FIG. 7 shows a RNA (SEQ ID NO:1) synthesized as disclosed herein containing a segment selectively labeled with $^{13}C/^{15}N$ nucleotides at residues 1-13, and HSQC 2D NMR spectra associated therewith.

The first 13 nucleotides at 5'-end of the 71 nt-riboswitch RNA were chosen to be $^{13}C^{15}N$ isotope labeled, and other residues are deuterated (RiboA-13 nt, the isotope labeled residues are shown in cyan in FIG. 7). In the initiation step, 28 µM T7 RNA polymerase were mixed with the same amount of immobilized DNA in 15 mL transcription buffer B for 10 minutes firstly, incubated with $^{13}C^{15}N$-rATP, $^{13}C^{15}N$-rGTP, and $^{13}C^{15}N$-rUTP at 37° C. for 15 min with gentle rotation (concentration ratios: $^{13}C^{15}N$-rATP:$^{13}C^{15}N$-rGTP:$^{13}C^{15}N$-rUTP:DNA=96:96:9.6:1. In the elongation step, added 15 mL transcription buffer D with deuterate-ATP, deuterate-CTP, deuterate-GTP, and deuterate-UTP to the beads used in initiation step and incubated @25 C for 15 min (deuterate-ATP:deuterate-CTP:deuterate-GTP:deuterate-UTP:DNA=14:13:10:21:1). The beads were then rinsed 3 times by 15 mL buffer C, and filtrate containing the final products was collected. In all the synthesis, the beads were rinsed by buffer C at least 3 times after incubation with rNTPs and buffer B in step 1 or buffer D in other steps. The overall yield for synthesizing RiboA-13 nt by this method is about 30%. The final products were purified by 15% denaturing PAGE before used as an NMR sample.

b. Labeling One Segment with $^{13}C^{15}N$-rNTPs (1) Six Step-Transcription to Label the L2 Loop with $^{13}C^{15}N$-rNTPs (20-26 Nucleotides)

Six steps were designed for preparing the NMR sample with $^{13}C^{15}N$-isotope labeled sequence shown in green in FIG. 8 (RiboA-L2). The initiation stage (step 1) is similar as described earlier, except the concentrations of DNA and T7 RNA polymerase are both 5 μM and the reaction volume is 30 mL. In the elongation stage (step 2 to 6), different combinations of rNTPs with 30 mL buffer D were added into the beads after the beads were rinsed 3 times by 30 mL buffer C. And the rNTPs used in the elongation stage are: rATP, rCTP and rUTP in step 2 (rATP:rCTP:rUTP:DNA=2:2:2:1), $^{13}C^{15}N$-rATP and $^{13}C^{15}N$-rGTP in step 3 ($^{13}C^{15}N$-rATP:$^{13}C^{15}N$-rGTP:DNA=1:1:1), $^{13}C^{15}N$-rATP and $^{13}C^{15}N$-rUTP in step 4 ($^{13}C^{15}N$-rATP:$^{13}C^{15}N$-rUTP:DNA=1:2:1), $^{13}C^{15}N$-rGTP in step 5 ($^{13}C^{15}N$-rGTP:DNA=2:1), and all four types of rNTPs in step 6 (rATP:rCTP:rGTP:rUTP:DNA=10:11:7:17:1). And the overall yield of producing RiboA-L2 by using the 6 step-transcription was close to 30%.

(2) Nine Step-Transcription to Label the L3 Loop (48-54 Nucleotides)

Figure 10:
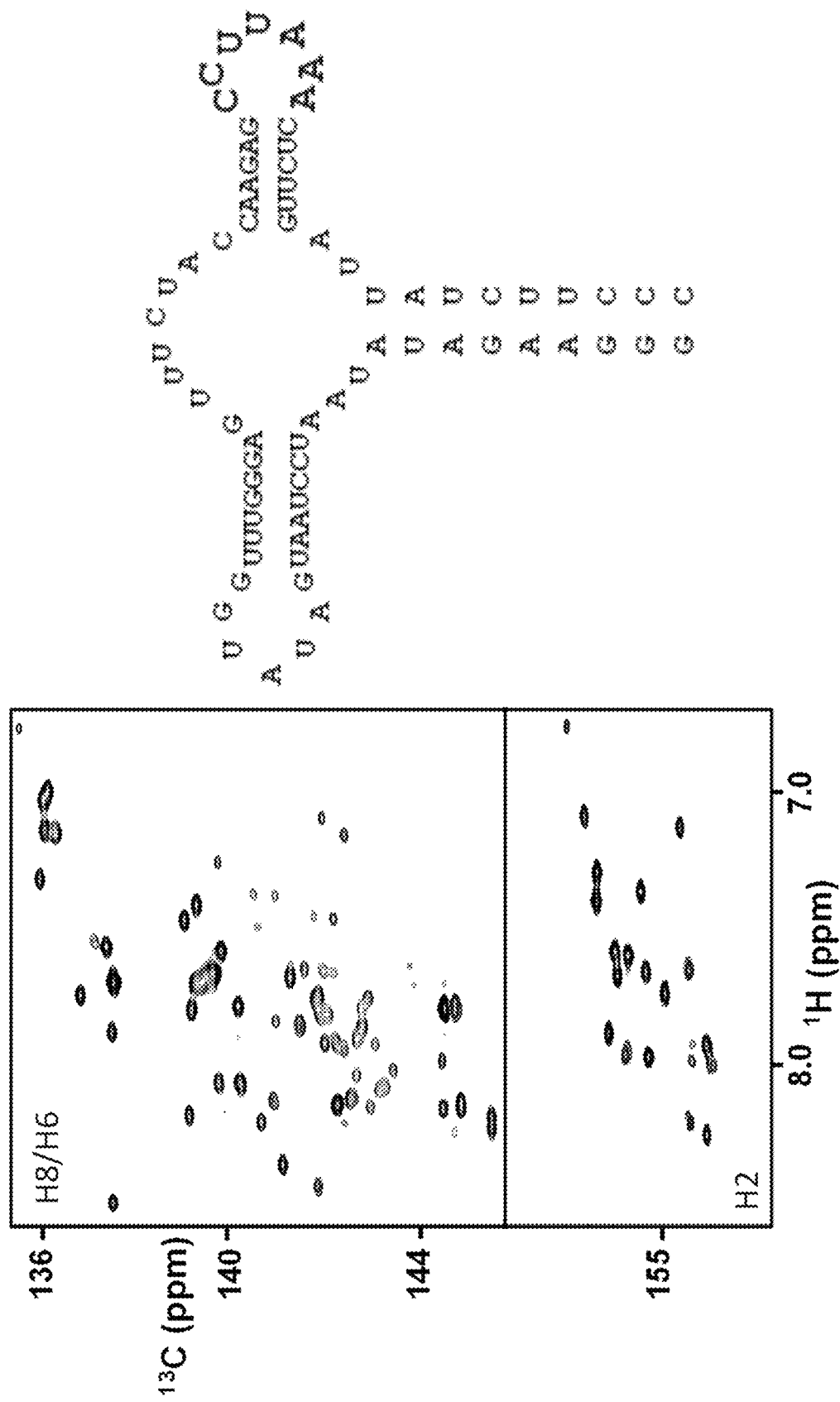
FIG. 10 shows a RNA (SEQ ID NO:1) synthesized as disclosed herein containing a segment selectively labeled with $^{13}C/^{15}N$ nucleotides at nt 48-55, and HSQC 2D NMR spectra associated therewith.

9 steps are needed for preparing the sample RiboA-L3, in which 7 nucleotides are $^{13}C^{15}N$ isotope labeled (shown in red in FIG. 10). Step 1 was pursued as described above, and the DNA concentration is 15 μM, and the total reaction volume is 90 mL, and the amount ratios among the added rATP, rGTP, rUTP, and DNA are the same as previously mentioned. The next 8 steps were proceeded similarly as the elongation step described earlier except that different rNTPs with 30 mL transcription buffer C were added in each step: rATP, rCTP, and rUTP in step 2 (rATP:rCTP:rUTP:DNA=2:2:2:1), rATP, rGTP, and rUTP in step 3 (rATP:rGTP:rUTP:DNA=3:7:8:1), rATP, rCTP, and rUTP in step 4 (rATP:rCTP:rUTP:DNA=3:3:1:1), rATP and rGTP in step 5 (rATP:rGTP:DNA=1:2:1), $^{13}C^{15}N$-rCTP and $^{13}C^{15}N$-rUTP in step 6 ($^{13}C^{15}N$-rCTP:$^{13}C^{15}N$-rUTP:DNA=2:2:1), $^{13}C^{15}N$-rATP in step 7 ($^{13}C^{15}N$-rATP:DNA=3:1), rCTP, rGTP, and rUTP in step 8 (rCTP:rGTP:rUTP:DNA=2:1:3:1), rATP, rCTP, and rUTP in step 9 (rATP:rCTP:rUTP:DNA=2:4:5:1). The yield of the 9 step-transcription was about 10%.

(3) Ten Step-Transcription to Label the L1 Loop (34-42 Nucleotides)

Figure 9:
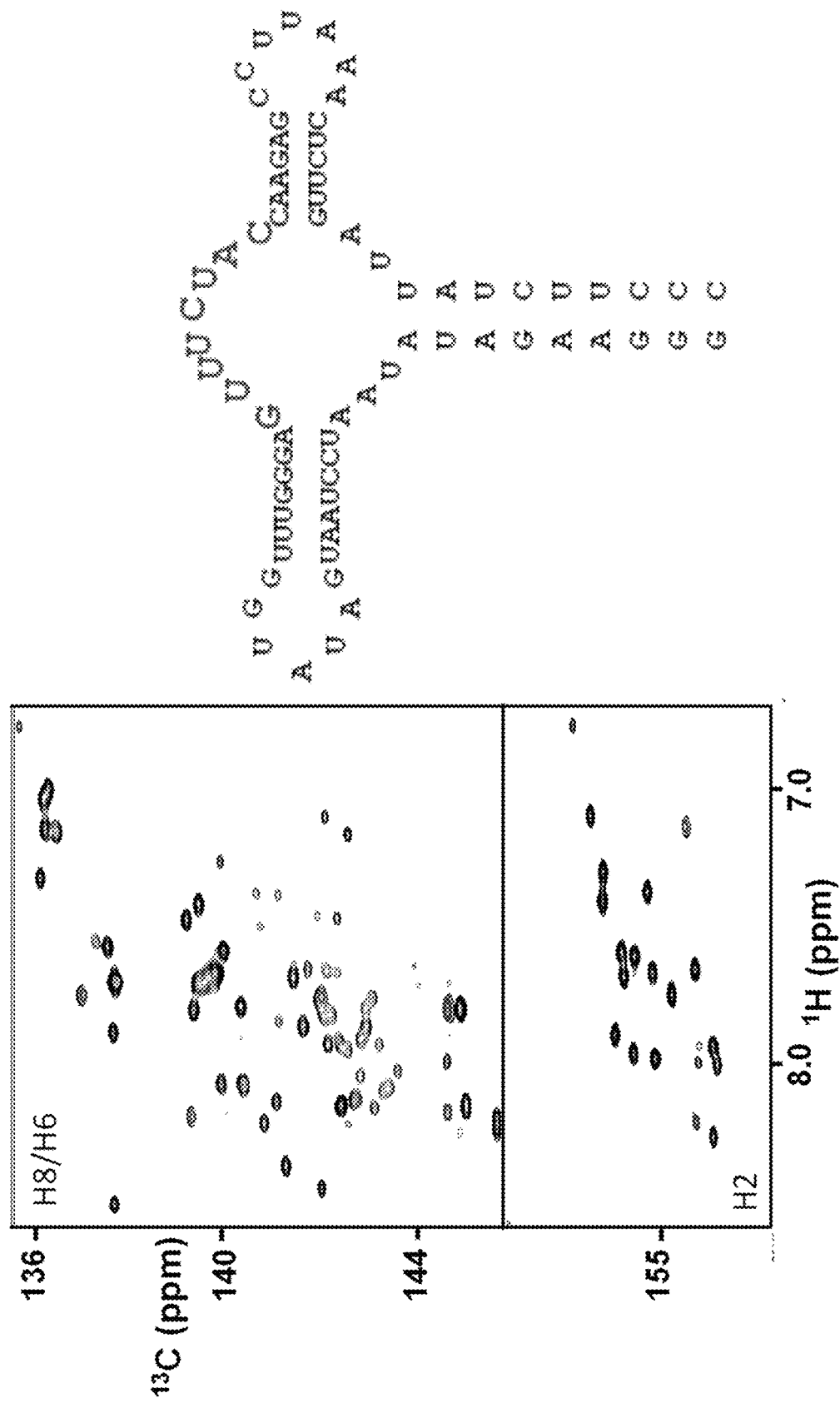
FIG. 9 shows a RNA (SEQ ID NO:1) synthesized as disclosed herein containing a segment selectively labeled with $^{13}C/^{15}N$ nucleotides at nt 34-41, and HSQC 2D NMR spectra associated therewith.

Ten steps were necessary for synthesizing RiboA-L1 (L1 loop is $^{13}C^{15}N$-isotope labeled, shown in blue in FIG. 9). DNA concentration used in initiation step was 5 μM, and the total reaction volume in each step was 152 mL. The added rNTPs and the ratios among rNTPs and DNA are listed as following: rATP, rGTP and rUTP (rATP:rGTP:rUTP:DNA=96:96:9.6:1) in step 1; rATP, rCTP and rUTP (rATP:rCTP:rUTP:DNA=2:2:2:1) in step 2; ATP and rGTP (rATP:rGTP:DNA=1:1:1) in step 3; rATP and rUTP (rATP:rUTP:DNA=1:2:1) in step 4; rGTP and rUTP (rGTP:rUTP:DNA=5:3:1) in step 5; rATP (rATP:DNA=1:1) in step 6; $^{13}C^{15}N$-rCTP, $^{13}C^{15}N$-rGTP and $^{13}C^{15}N$-rUTP ($^{13}C^{15}N$-rCTP:$^{13}C^{15}N$-rGTP:$^{13}C^{15}N$-rUTP:DNA=1:1:4:1) in step 7; $^{13}C^{15}N$-rATP ($^{13}C^{15}N$-rATP:DNA=1:1) in step 8; $^{13}C^{15}N$-rCTP ($^{13}C^{15}N$-rCTP:DNA=2:1) in step 9; rATP, rCTP, rGTP and rUTP (rATP:rCTP:rGTP:rUTP:DNA=8:8:3:10:1) in step 10. The yield of synthesizing the RibA-L1 sample by 10 step-transcription reactions was about 20%.

c. Labeling Two Segments with $^{13}C^{15}N$-rNTPs

To label both L2 and L3 loops, the whole synthesis are divided into 12 steps. In initiation step, different DNA concentration (28 μM) and the reaction volume in each step (70 mL) were used. The beads were rinsed similarly as described before after each step. Besides buffer B in step 1 and buffer C used in step 2 to step 12, the added rNTPs and the ratios among rNTPs and DNA are:

rATP, rGTP and rUTP (rATP:rGTP:rUTP:DNA=96:96:9.6:1) in step 1; rATP, rCTP and rUTP (rATP:rCTP:rUTP:DNA=2:2:2:1) in step 2; $^{13}C^{15}N$-rATP and $^{13}C^{15}N$-rGTP ($^{13}C^{15}N$-rATP:$^{13}C^{15}N$-rGTP:DNA=1:1:1) in step 3; $^{13}C^{15}N$-rATP and $^{13}C^{15}N$-rUTP ($^{13}C^{15}N$-ATP:$^{13}C^{15}N$-rUTP:DNA=1:2:1) in step 4; $^{13}C^{15}N$-rGTP ($^{13}C^{15}N$-rGTP:DNA=2:1) in step 5; rATP, rGTP and rUTP (rATP:rGTP:rUTP:DNA=1:4:6:1) in step 6; rATP, rCTP and rUTP (rATP:rCTP:rUTP:DNA=3:3:1:1) in step 7; rATP and rGTP (rATP:rGTP:DNA=1:2:1) in step 8; $^{13}C^{15}N$-rCTP and $^{13}C^{15}N$-rUTP ($^{13}C^{15}N$-rCTP:$^{13}C^{15}N$-rUTP:DNA=2:2:1) in step 9; $^{13}C^{15}N$-rATP ($^{13}C^{15}N$-rATP:DNA=3:1) in step 10; rCTP, rGTP, and rUTP (rCTP:rGTP:rUTP:DNA=2:1:3:1) in step 11, and rATP, rCTP, and rUTP in step 12 (rATP:rCTP:rUTP:DNA=2:4:5:1). The yield of the final product after the 11 steps was about 8%.

d. Labeling Specific Residues with Isotope-Enriched rNTPs

Figure 11:
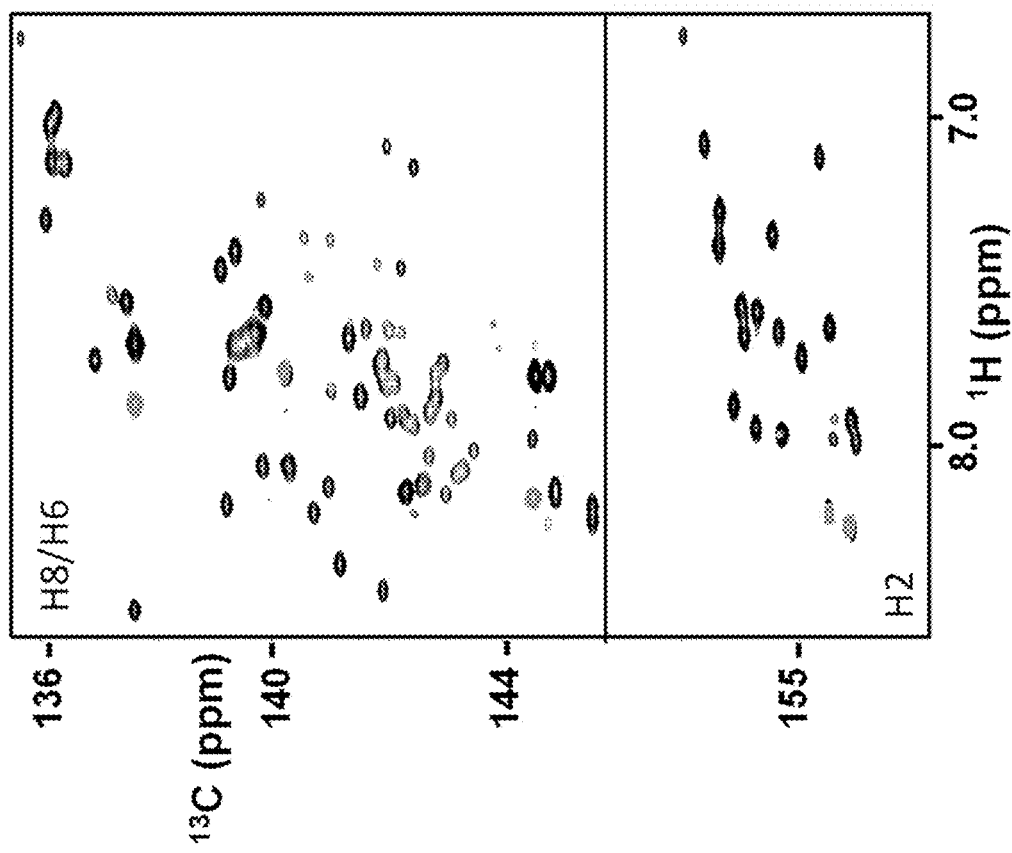
FIG. 11 shows a RNA (SEQ ID NO:1) synthesized as disclosed herein containing a segment selectively labeled with $^{13}C/^{15}N$ nucleotides at nt 21, 38, and 39, and HSQC 2D NMR spectra associated therewith. Discrete residues within the RNA are labeled.
Figure 12:
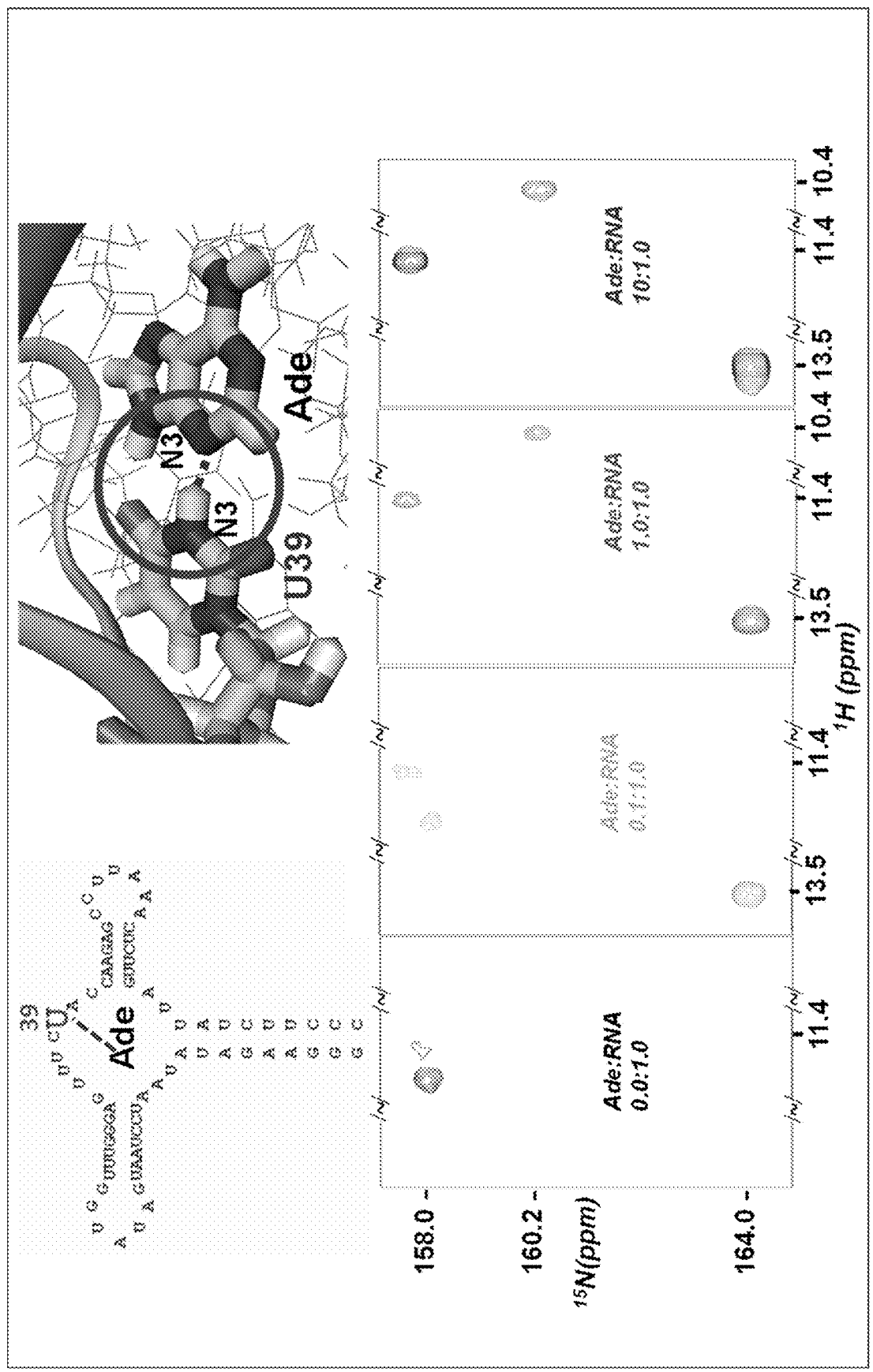
FIG. 12 shows how a selectively labeled RNA at a single position (nt 39) as synthesized herein can be used to identify multiple modes of adenine binding in a protein of interest.
Figure 13:
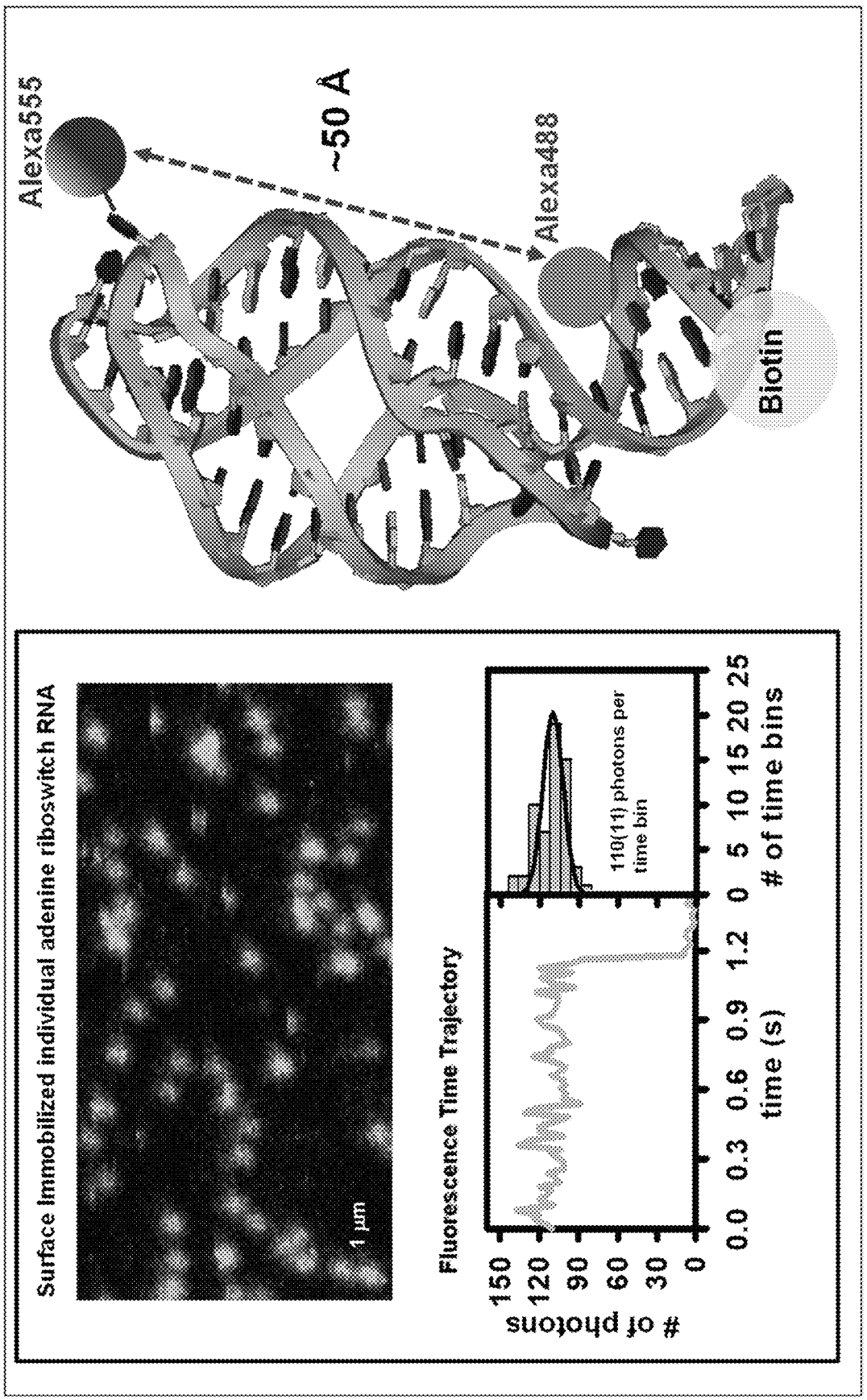
FIG. 13 shows how a selectively labeled RNA as synthesized herein can be used in sFRET analysis (nt U25-Alexa 555, C68-Alexa488, C71-Biotin).

Four residues, $^{21}$A, $^{38}$C and $^{39}$U (FIG. 11) were the targets for testing the capability of the step-wise transcription method in labeling single residues. The DNA concentration used in initiation step is 5 μM, and the total reaction volume was 152 mL. Eight more steps were processed, and the added rNTPs and the ratios among rNTPs in each step are listed below: rATP, rGTP and rUTP (rATP:rGTP:rUTP:DNA=96:96:9.6:1) in step 1; rATP, rCTP and rUTP (rATP:rCTP:rUTP:DNA=2:2:2:1) in step 2; $^{13}C^{15}N$-rATP and rGTP ($^{13}C^{15}N$-rATP:rGTP:DNA=1:1:1) in step 3; rATP, rGTP and rUTP (rATP:rGTP:rUTP:DNA=2:6:8:1) in step 4; $^{13}C^{15}N$-rCTP and $^{13}C^{15}N$-rUTP ($^{13}C^{15}N$-rCTP:$^{13}C^{15}N$-rUTP:DNA=1:1:1) in step 5; rATP, rCTP, and rGTP (rATP:rCTP:rGTP:DNA=4:4:2:1) in step 6; rATP, rCTP and rUTP (rATP:rCTP:rUTP:DNA=3:2:5:1) in step 7; $^{13}C^{15}N$-rGTP ($^{13}C^{15}N$-rGTP:DNA=1:1) in step 8; rATP, rCTP and rUTP (rATP:rCTP:rUTP:DNA=2:4:5:1) in step 9. The yield for the synthesis was about 10%.

e. RNA Yields

The following table shows yields of the above-described multi-step RNA synthesis for selectively labeling segments of RNA, as compared to RNA synthesis from a one-step transcription based on the same DNA template as above, either attached to a bead or free in solution.

| | | Overall transcription yield | | | | | Each step |
|---|---|---|---|---|---|---|---|
| Labeled positions | Needed steps | Based on template amount (before/after gel purification) | Based on rATP amount | Based on rCTP amount | Based on rGTP amount | Based on rUTP amount | transcription yield Based on template amount |
| $^1$G-$^{13}$U | 2 | 36.9%/23% | 6.7% | 36.9% | 4.9% | 29.5% | 60% |
| $^{51}$U | 5 | 32.0%/18% | 5.8% | 32.0% | 4.2% | 25.6% | 81% |
| $^{20}$A-$^{26}$G | 6 | 30.3%/22% | 5.5% | 30.3% | 4.0% | 24.2% | 82% |
| $^{48}$C-$^{54}$A | 9 | 10.2%/5.3% | 1.9% | 10.2% | 1.3% | 8.2% | 78% |

-continued

| Labeled positions | Needed steps | Overall transcription yield | | | | | Each step |
|---|---|---|---|---|---|---|---|
| | | Based on template amount (before/after gel purification) | Based on rATP amount | Based on rCTP amount | Based on rGTP amount | Based on rUTP amount | transcription yield Based on template amount |
| $^{21}$A, $^{38}$C, $^{39}$G, $^{60}$U | 9 | 12.2%/6.9% | 2.2% | 12.2% | 1.6% | 9.8% | 79% |
| $^{34}$G-$^{42}$C | 10 | 17.6%/12.5% | 3.2% | 17.6% | 2.3% | 14.1% | 84% |
| $^{20}$A-$^{26}$G, $^{48}$C-$^{54}$A | 12 | 8.5%/5.0% | 1.5% | 8.5% | 1.1% | 6.8% | 82% |
| None or all[a] | 1 | 13.3 (DNA-bead used) | 11.4% | 7.3% | 7.9% | 13.6% | 13.3 |
| None or all[b] | 1 | 756 (free DNA template used) | 28.7% | 18.7% | 20.1% | 34.5% | 756 |

Note:
[a]Use bead attached DNA as template. The 71-nt RNA is transcribed in a multiple cycles of one-step transcription reaction.
[b]Use free DNA (not bead attached) as template as in traditional liquid phase transcription and the 71-nt RNA was transcribed in a multiple cycles of one-step transcription reaction.

Example 2

Selective Labeling of RNA Segments

FIGS. 7-13 show examples of selectively labeled RNAs that were synthesized according to the method disclosed herein. The RNAs contain segments labeled with $^{13}$C/$^{15}$N nucleotides. The RNAs were detected using HSQC 2D NMR, which confirm that portions of the RNAs were selectively labeled.

Example 3

Method and Apparatus for Selectively Labeling RNA Segments

Figure 15:
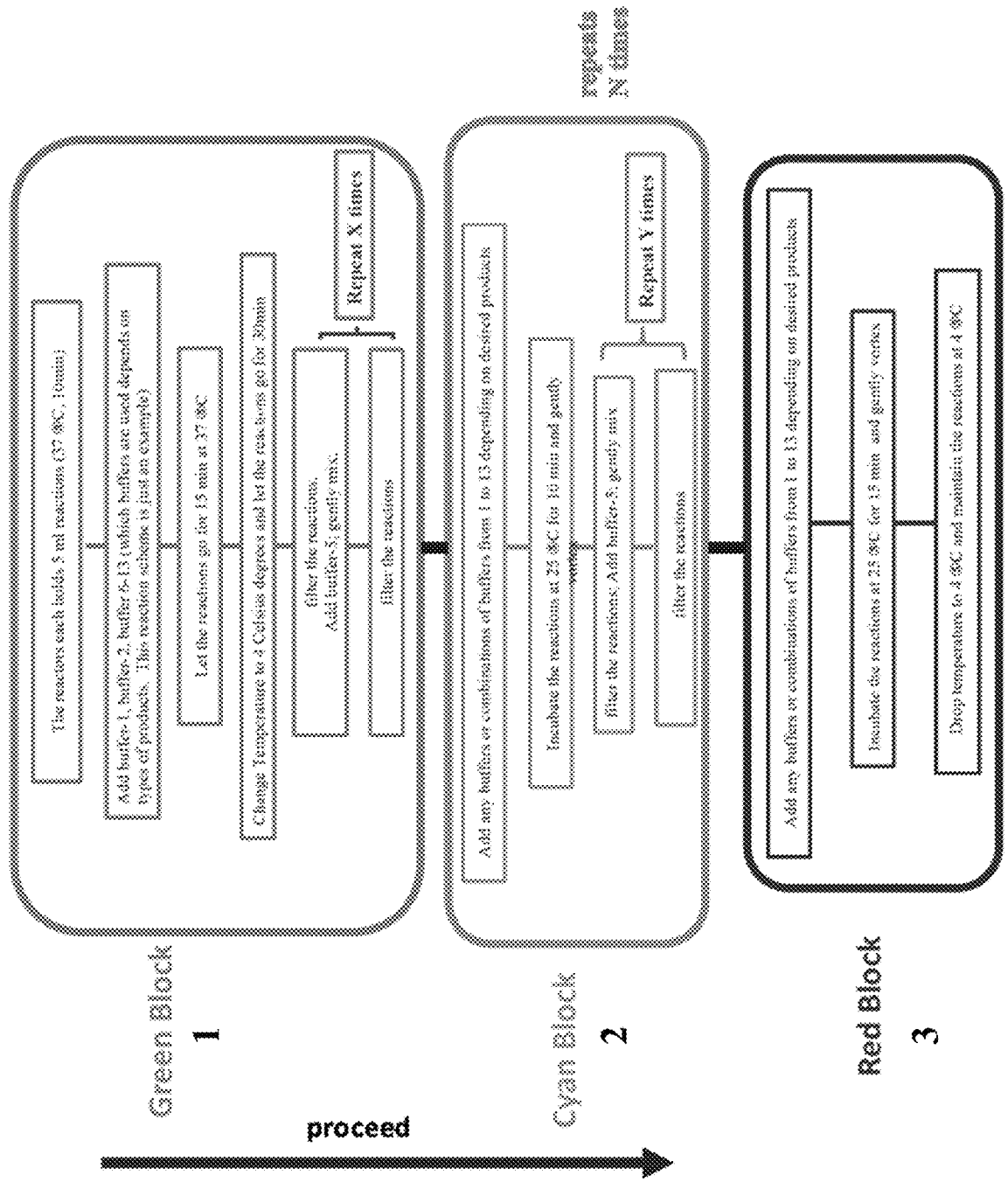
FIG. 15 shows the initiation (block 1), elongation (block 2), and termination (block 3) steps of an exemplary RNA synthesis reaction as described herein.

The example illustrates a RNA synthesis reaction for selectively labeling RNA segments, and an apparatus/automated platform for carrying out the method. FIG. 15 shows the initiation, elongation, and termination steps of the RNA synthesis reaction. FIG. 16 shows the layout of a deck of a robotic liquid handling platform for carrying out automated RNA synthesis, and FIGS. 17 and 18 shows further views of the automated platform. Buffers labeled 1, 2 and 4 are kept in 20 mL or 40 mL vials in racks of 2×4 (on left side of deck). Temperature control may not be needed. Buffers labeled 3 and 5 are kept in larger reservoirs kept off the deck with dedicated probes for their use only. No temperature control may be needed, and keeping dedicated probes eliminates any cross contamination. Reactants 6-13 (on right side of deck) are kept in 20 mL or 40 L vials in a rack of 2×4 and kept at 4° C. The deck in FIG. 15 has a heating vortexer mixing, but the vortexer can be replaced with a "tumbling" module for mixing. The tumbling module could rotate reactions 360° without creating bubbles. The deck may contain extra adaptors for parking extra buffers and/or filtration cartridges. Component 14 is a rack of 7 mL reactors/filtration cartridges, and component 15 is multiple racks for 40 mL collection vials, which are kept at 4° C.

The apparatus includes an instrument gripper that allows for the transportation of labware and assembly and disassembly of a filtration station automatically. The apparatus also includes an arm ("ARM 1"), a 6-way valve, syringe pumps, and solid phase extraction (SPE) components, including a SPE spot park, SPE vacuum lid, and SPE vacuum station. The apparatus also uses positive pressure, which can be regulated, with reactor/filtration vessels. The apparatus can also maintain samples under inert conditions using multi-channel probes that allow for dispensing of liquids and inert gas. The apparatus can accept input and export files for an internal laboratory information management system, which instruct the apparatus to perform the tasks for synthesizing RNA.

The apparatus carries out the synthesis reaction in FIG. 15 as follows. For block 1 (green block), (a) a bead suspension is provided in 6, 5 mL reactor/filtration vessels in a rack. The rack is temperature controlled on gentle vortexing or tumbling at 37° C. (b) The apparatus then adds a combination of buffers and reactants (buffer-1, buffer-2, and buffers/reactants 6-13) to the suspension defined by an input file. (c) The reaction is gently vortexed/tumbled at 37° C. for 15 minutes. (d) The apparatus then moves the rack of reaction vials to a temperature controlled position on the deck at 4° C. for 30 minutes. (e) The rack of reaction/filtration vessels is then moved to a filtration system at ambient temperature. (f) A buffer (buffer-5) is added by the apparatus, and (g) the reaction is gently mixed/tumbled. (h) The reactions are filtered to separate the solid phase from the liquid phase, and the filtrant goes to waste. (i) Steps (f)-(h) are repeated X (X=3-6) times, according to the input file.

For block 2 (cyan block), a rack of reaction vials is placed on a position on the deck at ambient temperature (25° C.). (a) The apparatus adds a combination of buffers and reactants (from buffer/reactants 1-13, as desired) according to the input file. (b) The reaction is incubated at ambient temperature for 10 minutes and gently vortexed/tumbled. (c) The reactor/filtration vessels are moved to the filtration station on the deck, which will be at ambient temperature. (d) The apparatus adds buffer-5 to the reaction vessels, and (e) gently mixes/tumbles the reaction. (f) The reaction is filtered to separate the solid and liquid phases, and the filtrant goes to waste. Steps (d)-(f) are repeated Y (Y=3-6) times according to the input file. Steps (a)-(g) are repeated N times according to the input file.

For block 3 (red block), reaction vessels are at ambient temperature. (a) The apparatus adds a combination of buffers and reactants (from buffers/reactants 1-13, as desired) according to the input file. (b) The reactions are incubated at ambient temperature for 15 minutes and gently vortexed/tumbled. (c) A collection of vials are sitting on 4° C. temperature controlled positions. While the reactions are incubating, the collection vials are moved from the 4° C. positions on the deck into position at the filtration station, which is at ambient temperature. (d) The apparatus moves the reactor/filtration vessels to the filtration station on the deck, which will be at ambient temperature. (e) The reactions are filtered at ambient temperature to separate the solid and liquid phases, and the solid phase is collected into the collection vials. (f) The collection vials are moved back to position on the deck to be kept at 4° C.

The invention claimed is:

1. A method for synthesizing a RNA, comprising performing an initiation stage, an elongation stage, and a termination stage, wherein:
 (a) the initiation stage comprises:
  (i) providing a solid phase comprising a DNA template, wherein the DNA is attached to a solid substrate;
  (ii) providing a first liquid phase comprising a RNA polymerase and ribonucleoside triphosphates (rNTPs);
  (iii) mixing the solid phase and first liquid phase;
  (iv) incubating the solid phase and first liquid phase at 4-37° C. for at least 10 minutes to initiate synthesis of the RNA;
  (v) pausing the RNA synthesis by incubating the solid phase and first liquid phase at 0-5° C. for at least 10 minutes, whereupon the solid phase comprises the RNA polymerase and the RNA being synthesized; and
  (vi) separating the solid phase from the first liquid phase;
 (b) the elongation stage comprises:
  (i) providing a second liquid phase comprising rNTPs;
  (ii) mixing the solid phase and second liquid phase;
  (iii) incubating the solid phase and second liquid phase at 4-37° C. for at least 10 minutes to elongate the RNA;
  (iv) pausing the RNA synthesis by incubating the solid phase and second liquid phase at 0-5° C. for at least 10 minutes;
  (v) separating the solid phase from the second liquid phase; and
  (vi) repeating steps (i)-(v) of part (b) n times, wherein n is equal to 1-100, and wherein the rNTPs in the second liquid phase are the same or different in each repeat;
 (c) the termination stage comprises:
  (i) providing a third liquid phase comprising rNTPs;
  (ii) mixing the solid phase with the third liquid phase;
  (iii) incubating the solid phase and third liquid phase at 4-37° C. for at least 10 minutes; and
  (iv) pausing the RNA synthesis by incubating the solid phase and third liquid phase at 0° C. for at least 10 minutes;
 wherein steps (a)-(c) are repeated m times, wherein m is equal to 1-100, and wherein rNTPs of at least one of the first liquid phase, the second liquid phase, or third liquid phase comprise a label.

2. The method of claim 1, wherein the solid substrate is a bead comprising a gel, glass, or a synthetic polymer.

3. The method of claim 2, wherein the bead has a diameter of 5-100 µm.

4. The method of claim 1, wherein the RNA polymerase is T7 RNA polymerase.

5. The method of claim 1, wherein the label is selected from the group consisting of $^{13}C/^{15}N$, $^{2}H$, Cy3, Cy5, a fluorophore, a heavy atom, and a chemical modification.

* * * * *